(12) United States Patent
Muto et al.

(10) Patent No.: US 11,606,514 B2
(45) Date of Patent: Mar. 14, 2023

(54) SIGNAL PROCESSING CIRCUIT AND SIGNAL PROCESSING METHOD

(71) Applicant: CANON KABUSHIKI KAISHA, Tokyo (JP)

(72) Inventors: Hiroyuki Muto, Kanagawa (JP); Yusuke Yamamoto, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 10 days.

(21) Appl. No.: 17/141,548

(22) Filed: Jan. 5, 2021

(65) Prior Publication Data
US 2021/0227154 A1 Jul. 22, 2021

(30) Foreign Application Priority Data
Jan. 17, 2020 (JP) .............................. JP2020-006220

(51) Int. Cl.
*H04N 5/32* (2006.01)
*B60R 16/023* (2006.01)
*H03M 1/06* (2006.01)

(52) U.S. Cl.
CPC ........... *H04N 5/32* (2013.01); *B60R 16/0231* (2013.01); *H03M 1/0602* (2013.01)

(58) Field of Classification Search
CPC .... H04N 5/32; B60R 16/0231; H03M 1/0602
See application file for complete search history.

(56) References Cited

U.S. PATENT DOCUMENTS

| 5,677,940 A * | 10/1997 | Suzuki | H04N 5/32 378/38 |
| 2002/0004636 A1* | 1/2002 | Tsubata | A61B 8/02 600/502 |
| 2002/0027962 A1* | 3/2002 | Muller | H03G 5/005 375/229 |
| 2004/0223582 A1* | 11/2004 | Kamimura | G16H 40/63 378/4 |
| 2005/0024998 A1* | 2/2005 | Inoue | G11B 20/1816 |

(Continued)

FOREIGN PATENT DOCUMENTS

JP 3565973 B2 9/2004
JP 2016-61614 A 4/2016
(Continued)

OTHER PUBLICATIONS

European Search Report dated Jun. 21, 2021 in corresponding European application No. 20217500.6.

*Primary Examiner* — Shawn S An
(74) *Attorney, Agent, or Firm* — Venable LLP

(57) ABSTRACT

A signal processing circuit includes a detection unit configured to detect generation of a peak in an analog signal based on an input of a photon, an A/D conversion unit configured to perform A/D conversion of a signal value into digital data of bits by determining a value of each of the bits from an upper bit to a lower bit, and a control unit configured to control the A/D conversion unit so that, in a case in which the generation of a second peak of the analog signal is detected during the A/D conversion of a signal value of a first peak of the analog signal, the A/D conversion of the signal value of the first peak will be interrupted and the A/D conversion of a signal value of the second peak will be started.

17 Claims, 18 Drawing Sheets

(56) References Cited

U.S. PATENT DOCUMENTS

| | | | | |
|---|---|---|---|---|
| 2008/0106748 A1* | 5/2008 | Tsukahara | .......... | H04N 1/40056 358/445 |
| 2009/0322950 A1* | 12/2009 | Mitsunaka | ............... | H04B 1/28 348/731 |
| 2015/0085985 A1* | 3/2015 | Funaki | ................... | H04N 5/378 378/98 |
| 2016/0077148 A1* | 3/2016 | Kimura | .............. | G01R 31/2635 702/58 |

FOREIGN PATENT DOCUMENTS

| | | | |
|---|---|---|---|
| JP | 2019-87873 A | 6/2019 | |
| JP | 2019-219251 A | 12/2019 | |

\* cited by examiner

FIG. 14

| PEAK VALUE (1401) | ELAPSED TIME (DETERMINED NUMBER OF BITS) (1402) | CORRECTION AMOUNT (1403) |
|---|---|---|
| 1000000 | 1 | ... |
| | 2 | ... |
| | ... | ... |
| | 8 | 0 |
| 1100000 | 1 | ... |
| | 2 | ... |
| | ... | ... |
| | 8 | 0 |
| ... | ... | ... |

SIGNAL PROCESSING CIRCUIT AND SIGNAL PROCESSING METHOD

BACKGROUND OF THE INVENTION

Field of the Invention

The disclosure relates to a signal processing circuit and a signal processing method.

Description of the Related Art

A light detection method called photon counting that detects light by counting the number of photons is known. A photon-counting CT (Computed Tomography) apparatus is an example of an apparatus that uses this photon counting method. A CT apparatus employing this method sorts electrical signals (pulses) generated by an X-ray detector in accordance with energy (wavelength) regions, and performs signal processing to count the number of pulses in each energy region for each predetermined time. A tomographic image of an object is generated based on the result of this signal processing. Japanese Patent Laid-Open No. 2016-61614 discloses a technique in which A/D conversion is performed after an electrical signal generated by an X-ray detector has been amplified/shaped, and the number of pulses is counted for each peak value. Since photons are input randomly, it may cause a plurality of pulse signals to overlap. This kind of phenomenon is called a pileup. Japanese Patent Laid-Open No. 2016-61614 discloses that, in a case of a pileup, a plurality of capacitors will be used to hold the signal values of the plurality of peaks, and A/D conversion of these signal values will be performed by shifting the timing.

SUMMARY OF THE INVENTION

In consideration of the above problem, there provided a signal processing circuit comprising: a detection unit configured to detect generation of a peak in an analog signal whose signal value changes in accordance with an input of a photon; an A/D conversion unit configured to perform A/D conversion of a signal value of a peak of the analog signal into digital data of a plurality of bits by determining a value of each of the plurality of bits from an upper bit to a lower bit; and a control unit configured to control the A/D conversion unit so that, in a case in which the generation of a second peak of the analog signal is detected during a period in which the A/D conversion of a signal value of a first peak of the analog signal is being performed, the A/D conversion of the signal value of the first peak will be interrupted and the A/D conversion of a signal value of the second peak will be started.

Further features of the present invention will become apparent from the following description of exemplary embodiments (with reference to the attached drawings).

BRIEF DESCRIPTION OF THE DRAWINGS

FIG. 14 is a view for explaining an example of a table for calculating a correction amount according to the third embodiment;

DESCRIPTION OF THE EMBODIMENTS

Figure 1:
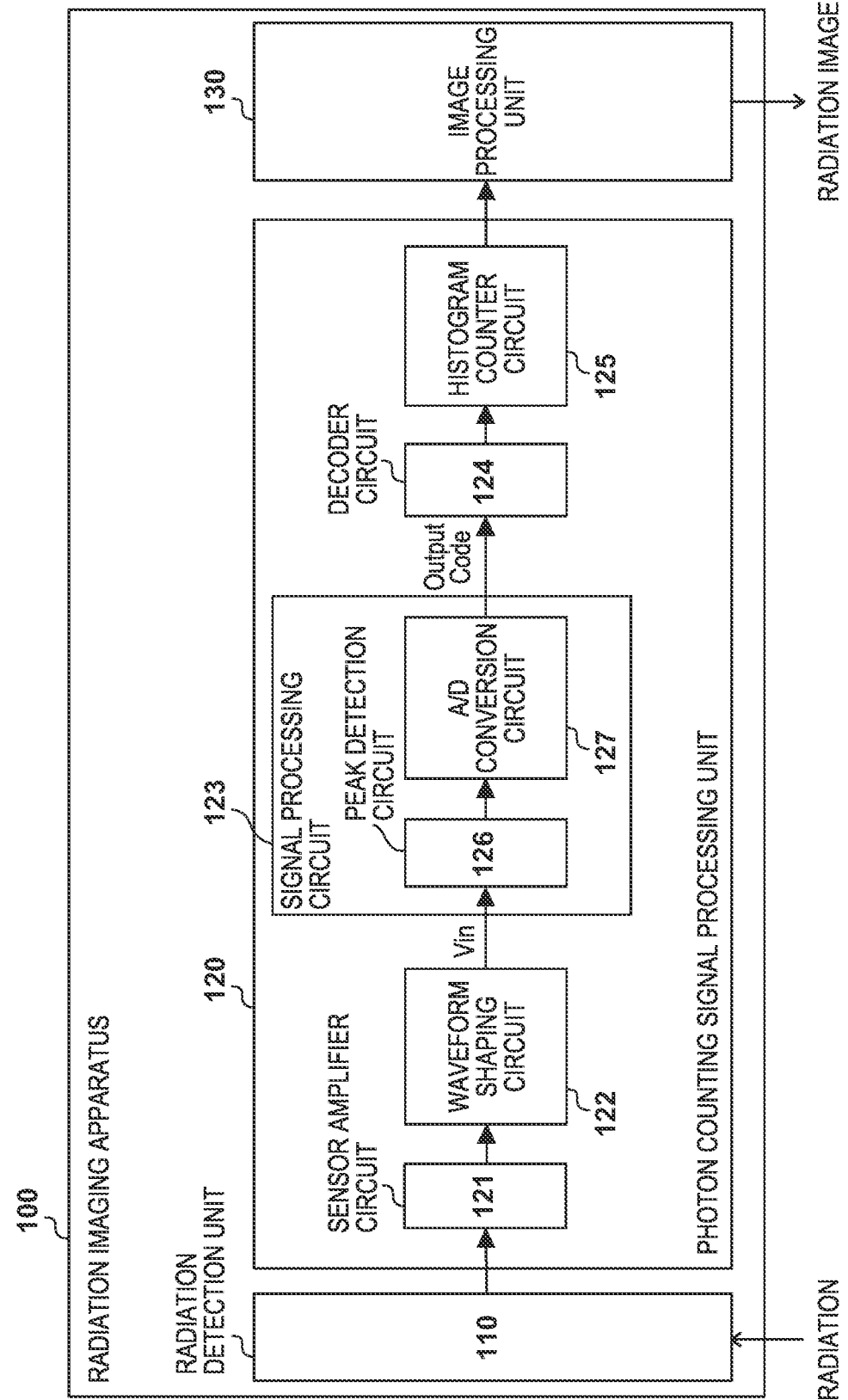
FIG. 1 is a block diagram for explaining an example of the arrangement of a radiation imaging apparatus according to the first embodiment.

Hereinafter, embodiments will be described in detail with reference to the attached drawings. Note, the following embodiments are not intended to limit the scope of the claimed invention. Multiple features are described in the embodiments, but limitation is not made to an invention that requires all such features, and multiple such features may be combined as appropriate. Furthermore, in the attached drawings, the same reference numerals are given to the same or similar configurations, and redundant description thereof is omitted.

In a plurality of embodiments to be described hereinafter, radiation can include X-rays, α-rays, β-rays, γ-rays, cosmic rays, and neutron beams.

The technique disclosed in Japanese Patent Laid-Open No. 2016-61614 requires a plurality of capacitors to hold signal values of a plurality of peaks. As a result, the circuit scale increases. This specification will describe a technique that can improve the counting performance by a simple arrangement.

First Embodiment

[Overall Arrangement of Radiation Imaging Apparatus]

An example of the arrangement of a radiation imaging apparatus 100 according to the first embodiment will be described with reference to FIG. 1. The radiation imaging apparatus 100 is an apparatus that generates a radiation image corresponding to the radiation that entered the radiation imaging apparatus 100. The radiation imaging apparatus 100 may be, for example, a CT apparatus.

The radiation imaging apparatus 100 includes a radiation detection unit 110, a photon counting signal processing unit 120, and an image processing unit 130. The photon counting signal processing unit 120 includes a sensor amplifier circuit 121, a waveform shaping circuit 122, a signal processing circuit 123, a decoder circuit 124, and a histogram counter circuit 125. Only the components used in the following description are shown in FIG. 1, and other components are omitted. Components that are not shown in FIG. 1 can be similar to those of a related art.

The radiation detection unit 110 converts radiation photons (for example, X-ray photons) that entered the radiation imaging apparatus 100 into electrical signals (microcurrent pulses). More specifically, the radiation detection unit 110 generates an electrical pulse signal which has a peak level corresponding to the energy (wavelength) of the input radiation photons. Radiation photons will randomly enter the radiation detection unit. The radiation detection unit 110 may be a direct radiation detection unit that directly converts the input radiation photons into charges or may be an indirect radiation detection unit that coverts radiation into light by a scintillator which has a fluorescent characteristic and detects this converted light.

The sensor amplifier circuit 121 amplifies a microcurrent signal supplied from the radiation detection unit 110 and converts this signal into a voltage signal. The waveform shaping circuit 122 performs waveform shaping by executing filter processing on the voltage signal from the sensor amplifier circuit 121, and supplies, to the signal processing circuit 123, a voltage signal Vin that has been shaped. The voltage signal Vin is an analog signal that changes in accordance with the input of the radiation photons. The signal processing circuit 123 detects the generation of a peak in the voltage signal Vin, and performs A/D (analog/digital) conversion to convert the signal value of the peak into digital data Output Code which is formed by a plurality of bits. The digital data may also be referred to as a digital code.

The decoder circuit 124 converts the digital data (8-bit width data if the ADC resolution is of 8 bits) that has undergone the A/D conversion into a one-hot signal (a signal in which only 1 bit is high and the remaining bits are low among 2^8=256 bits). For example, the AD-converted 8-bit data is converted into a 256-bit pulse signal. This processing is performed to count the number of pulses in each bin in the histogram counter circuit 125 of a subsequent stage.

The histogram counter circuit 125 counts, based on the output from the decoder circuit 124, the number of pulses detected for each level after the A/D conversion. As a result, the histogram counter circuit 125 can count the number of radiation photons that entered each energy region. The image processing unit 130 generates a radiation image by performing image processing and image formation based on count values from the histogram counter circuit 125. The radiation image is, for example, a cross-sectional image of an object.

[Arrangement of Signal Processing Circuit]

Figure 2:
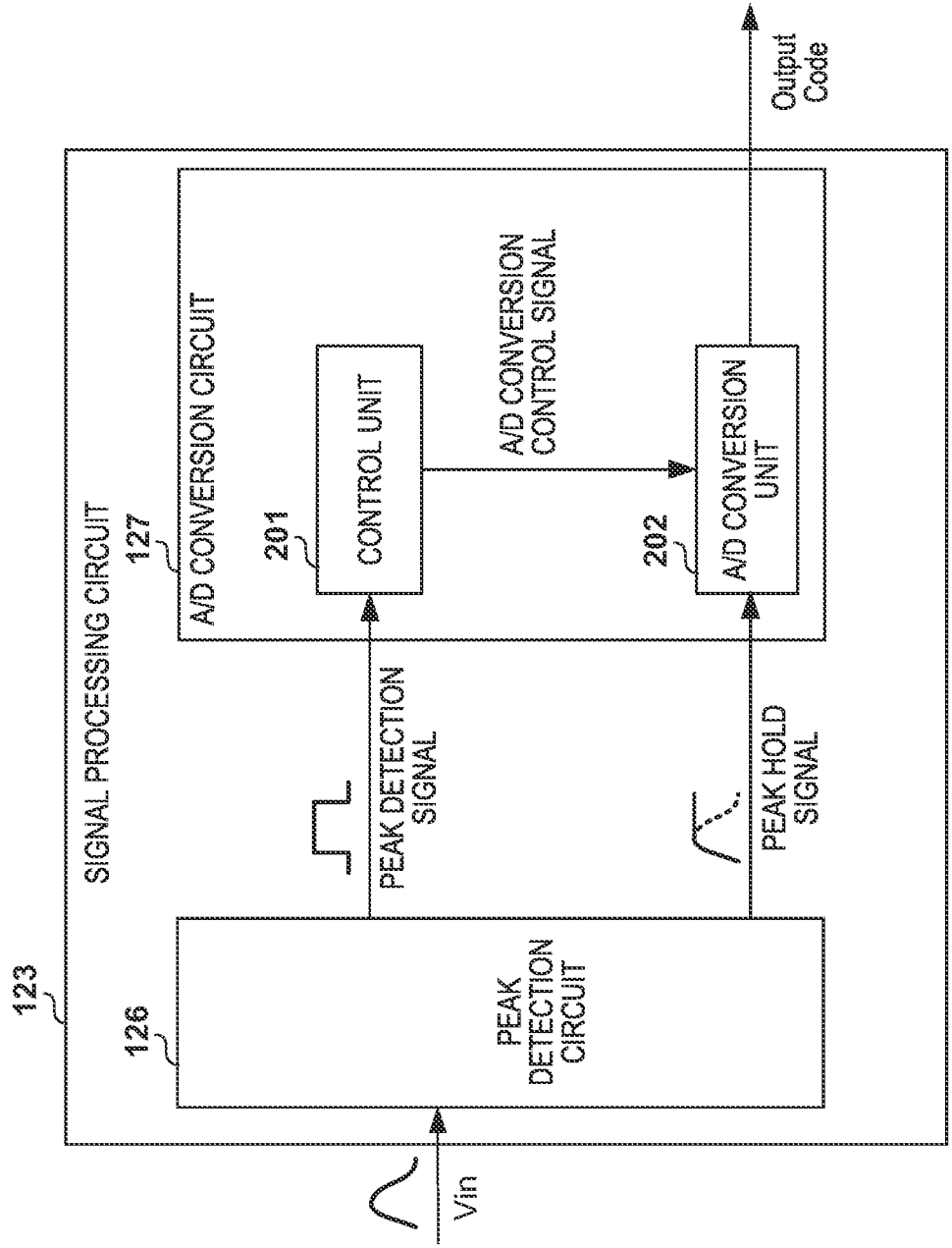
FIG. 2 is a block diagram for explaining an example of the arrangement of a signal processing circuit according to the first embodiment.

An example of the arrangement of the signal processing circuit 123 will be described with reference to FIG. 2. The signal processing circuit 123 includes a peak detection circuit 126 and an A/D conversion circuit 127. The peak detection circuit 126 detects the peak of the voltage signal Vin supplied from the waveform shaping circuit 122 and outputs a peak detection signal (digital signal) that indicates the detection of the generation of the peak. The peak detection circuit 126 also holds the signal value of the peak of the voltage signal Vin, and outputs this signal value as a peak hold signal (analog signal). The signal value of the peak may also be referred to as a peak value. The A/D conversion circuit 127 generates the above-described digital data Output Code based on the peak detection signal and the peak hold signal.

The A/D conversion circuit 127 includes a control unit 201 and an A/D conversion unit 202. The control unit 201 generates an A/D conversion control signal based the peak detection signal output as a trigger from the peak detection circuit 126. This A/D conversion control signal is a signal that controls the start and the end of the A/D conversion by the A/D conversion unit 202. The A/D conversion unit 202 is triggered by the generated A/D conversion control signal to perform A/D conversion on the peak hold signal. In a case in which a peak detection signal indicating the detection of the generation of a subsequent peak is supplied during the A/D conversion of the peak hold signal, the control unit 201 will interrupt the A/D conversion that is currently being executed. In this case, the A/D conversion unit 202 can immediately start the next A/D conversion operation. After the end of the A/D conversion, the A/D conversion unit 202 outputs the digital data Output Code as a result of the A/D conversion.

As described above, in a case in which the generation of a next peak is detected during an A/D conversion operation, the signal processing circuit 123 can interrupt the A/D conversion before all of the bits of the digital data are determined based on the A/D conversion control signal of the control unit 201. Hence, the signal processing circuit 123 can change the precision of the resolution of the A/D conversion in accordance with the peak detection interval of the voltage signal Vin.

[More Specific Arrangement of Signal Processing Circuit]

Figure 3:
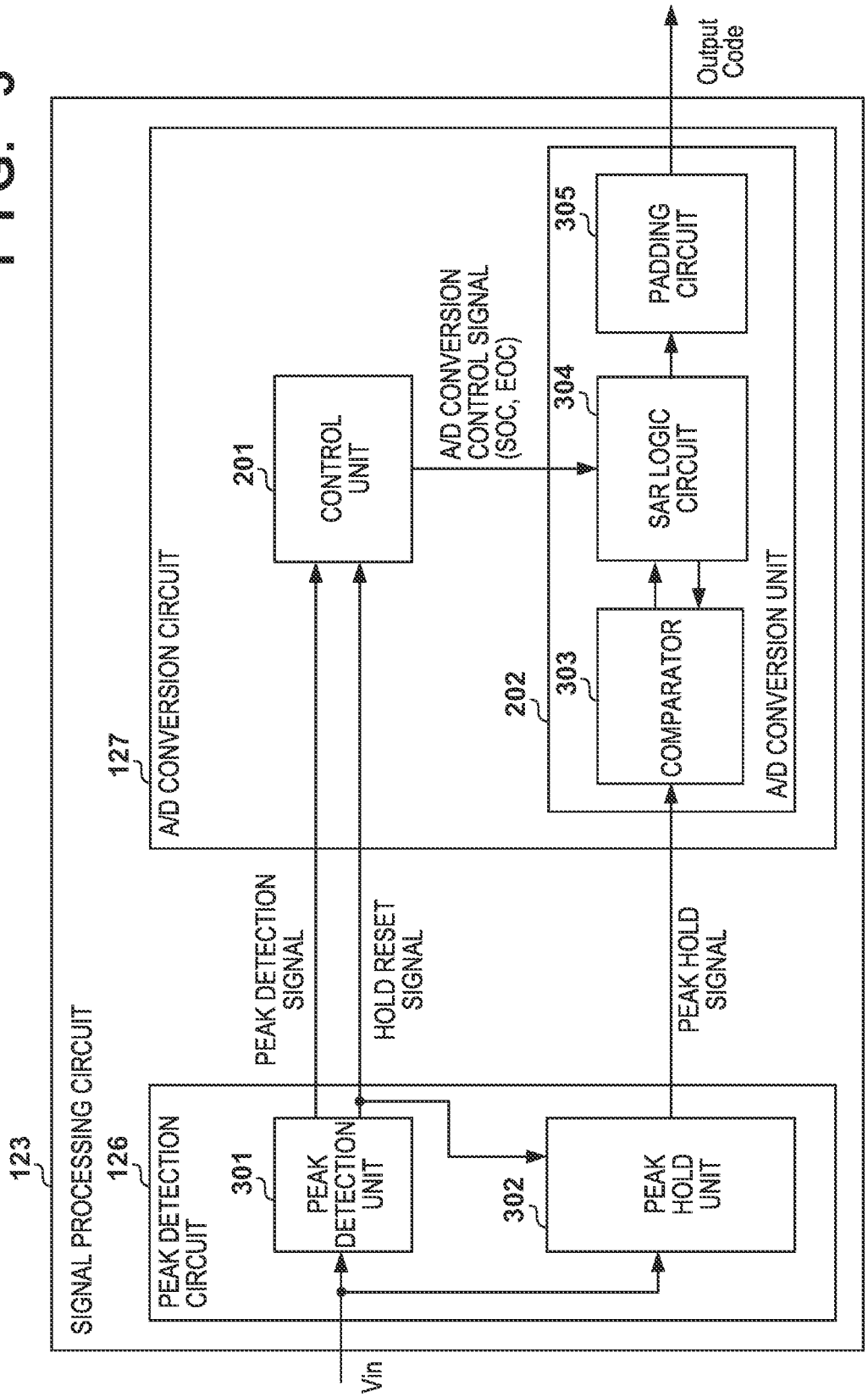
FIG. 3 is a block diagram for explaining an example of the detailed arrangement of the signal processing circuit according to the first embodiment.

An example of the more specific arrangement of the signal processing circuit 123 will be described with reference to FIG. 3. A peak detection circuit 126 includes a peak detection unit 301 and a peak hold unit 302. The peak detection unit 301 detects the generation of a peak in the voltage signal Vin, and generates a peak detection signal (digital signal) indicating that the peak has been generated. The peak detection unit 301 supplies the peak detection signal to the A/D conversion circuit 127. Furthermore, the peak detection unit 301 generates a hold reset signal (digital signal) that controls the peak hold state of the peak hold unit 302. The peak detection unit 301 supplies the hold reset signal to the A/D conversion circuit 127 and the peak hold unit 302.

The peak detection unit 301 sets the hold reset signal to high during a period in which the peak hold unit 302 is to hold the peak value, and sets the hold reset signal to low in other periods. The peak detection unit 301 keeps the hold reset signal at high level for a sufficient time until the A/D conversion (to be described later) is completed.

The peak hold unit 302 holds the signal value of the voltage signal Vin based on the hold reset signal, and supplies the voltage signal Vin corresponding to the held signal value as the peak hold signal to the A/D conversion circuit 127. More specifically, while the hold reset signal is high, the peak hold unit 302 outputs the maximum value of the voltage signal Vin as the peak hold signal obtained from a point of time in which the hold reset signal goes high to the (current) point of time of the output. Hence, subsequently, when the voltage signal Vin reaches the peak while the hold reset signal is high, the peak hold unit 302 will hold the peak value and supply the peak value to the A/D conversion circuit 127. The peak hold unit 302 performs an operation to follow the voltage signal Vin while the hold reset signal is low. Hence, when the hold reset signal has changed from high to low, the peak hold unit 302 will cancel the hold state of the peak value.

[More Specific Arrangement of Peak Detection Circuit]

Figure 4:
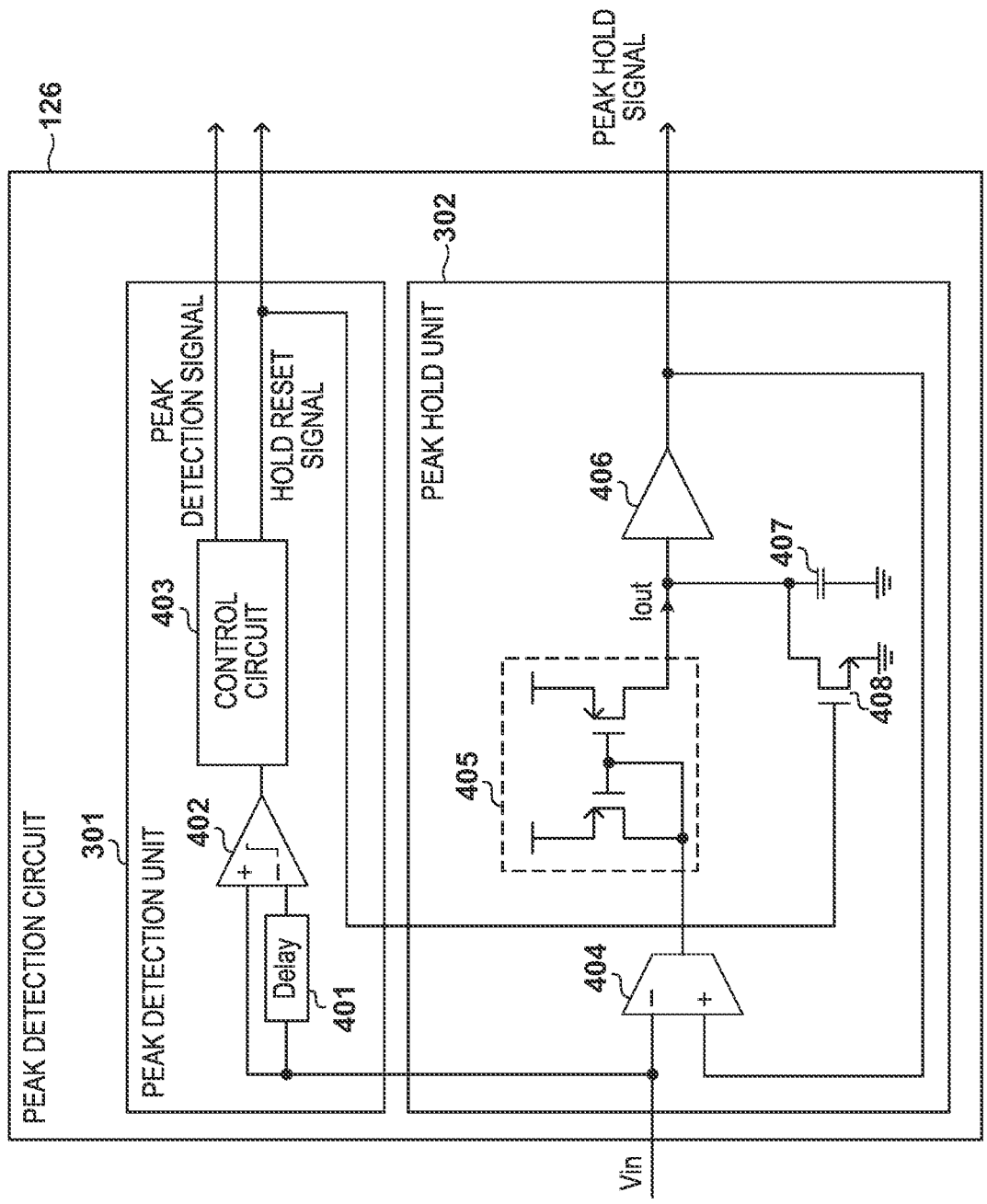
FIG. 4 is a block diagram for explaining an example of the arrangement of a peak detection circuit according to the first embodiment.

An example of the more specific arrangement of the peak detection circuit 126 will be described with reference to FIG. 4. The peak detection unit 301 includes a delay circuit 401, a comparator circuit 402, and a control circuit 403. The voltage signal Vin (that is, the input signal to the peak detection circuit 126) is supplied to a non-inverting input terminal as well as an inverting input terminal via the delay circuit 401 of the comparator circuit 402. The comparator circuit 402 supplies the difference obtained from these terminals to the control circuit 403. Hence, a positive value signal will be supplied to the control circuit 403 while the voltage signal Vin increases, and a negative value signal will be supplied to the control circuit 403 while the voltage signal Vin decreases.

The control circuit 403 sets the peak detection signal to high when the signal from the comparator circuit 402 is a positive signal, and sets the peak detection signal to low when the signal from the comparator circuit 402 is a negative signal. In addition, the control circuit 403 may keep the signal level at the level up to that point when the signal from the comparator circuit 402 is 0. The leading edge (when changing from low to high) of the peak detection signal indicates that the voltage signal Vin has started to increase and will subsequently reach the peak. The falling edge (when changing from high to low) of the peak detection signal indicates that the voltage signal has reached the peak. In the subsequent explanation, the peak detection unit 301 detects the generation of the peak based on the increase of the voltage signal Vin. Alternatively, the peak detection unit 301 may detect the generation of the peak based on the fact that voltage signal Vin has actually reached a peak. Either case can be expressed as the detection of the generation of the peak.

In a case in which the signal from the comparator circuit 402 has changed from a negative signal to a positive signal, the control circuit 403 will change the hold reset signal to high. After the signal from the comparator circuit 402 has changed from a negative signal to a positive signal, the control circuit 403 will subsequently set the hold reset signal to low after keeping the hold reset signal high for a predetermined time. The period in which the hold reset signal is kept high is set in advance so that the period will be longer than the time required for the A/D conversion of the peak value. As will be described later, in a case in which the A/D conversion is to be interrupted, the control circuit 403 will temporarily change the hold reset signal to low even if the set period has not elapsed.

The peak hold unit 302 includes a transconductance amplifier 404, a current mirror circuit 405, a buffer circuit 406, a hold capacitor 407, and a reset switch 408. The input signal (that is, the voltage signal Vin) to the peak hold unit 302 is supplied to the inverting input terminal of the transconductance amplifier 404. The output signal (that is, the peak hold signal) from the peak hold unit 302 is supplied to the non-inverting input terminal of the transconductance amplifier 404. When the voltage signal Vin exceeds the peak hold signal, a current Iout whose value corresponds to the voltage signal Vin is output from the current mirror circuit 405. The current Iout is output as the peak hold signal from the peak hold unit 302 via the buffer circuit 406 and is supplied to the hold capacitor 407. On the other hand, when the voltage signal Vin becomes below the peak hold signal, the current Iout from the current mirror circuit 405 is 0. Hence, during a period in which the voltage signal Vin is lower than the peak hold signal, the value of the peak hold signal will correspond to the voltage held by the hold capacitor 407.

The reset switch 408 is set to a non-conductive state when the hold reset signal is high, and is set to a conductive state when the hold reset signal is low. When the reset switch 408 is set to a conductive state, the charges held in the hold capacitor 407 are reset.

[More Specific Arrangement of A/D Conversion Circuit]

An example of the arrangement of the A/D conversion circuit 127 will be described with reference to FIG. 3 again. The control unit 201 generates A/D conversion control signals based on the peak detection signal and the hold reset signal. The A/D conversion control signals include a signal SOC (Start of Conversion) which instructs the start of the A/D conversion and a signal EOC (End of Conversion) which instructs the end of A/D conversion. The control unit 201 supplies, as the signal SOC, a signal which has the same waveform as the peak detection signal to the A/D conversion unit 202. When ending the A/D conversion, the control unit 201 will change the signal EOC to high. After the signal EOC has been changed to high, the control unit 201 will change the signal EOC back to low after a predetermined time has elapsed to make the next end instruction.

The A/D conversion unit 202 performs A/D conversion on the peak hold signal (analog signal) to convert the peak hold signal into digital data which is made of a plurality of bits. The A/D conversion unit 202 determines the plurality of bits of digital data sequentially from the upper bit to the lower bit. This A/D conversion unit 202 can be either an SAR (Successive Approximation Register) A/D conversion circuit, a cyclic A/D conversion circuit, or a pipeline A/D conversion circuit. A case in which the A/D conversion unit 202 is an SAR A/D conversion circuit will be described hereinafter.

The A/D conversion unit 202 includes a comparator 303 and an SAR logic circuit 304. The A/D conversion unit 202 initializes the A/D conversion unit 202 by resetting the SAR logic circuit 304 in response to the signal SOC changing from low to high. As a result, the preparation to start the A/D conversion is completed. Subsequently, the A/D conversion unit 202 starts the A/D conversion of the peak hold signal in accordance with the signal SOC being changed from low to high. The A/D conversion unit 202 may self-generate an A/D clock signal in the SAR logic circuit 304. The A/D conversion unit 202 may also have a self-clocking arrangement that self-generates the A/D clock signal in this manner. The comparator 303 may be a dynamic comparator or a capacitance DAC (Digital-to-Analog Converter).

When the A/D conversion is started, the A/D conversion unit 202 determines each bit of the digital data by binary search. More specifically, the SAR logic circuit 304 compares the peak hold signal with the reference voltage from the comparator 303. In a case in which the voltage of the peak hold signal is higher than the reference voltage, the SAR logic circuit 304 will set the target bit to 1 and will set the target bit to 0 in other cases. The SAR logic circuit 304 issues an instruction to the comparator 303 so that a reference voltage for determining a subsequent bit will be supplied for each bit determination operation.

A padding circuit 305 pads each undetermined bit when the A/D conversion is interrupted. The padding circuit 305 may set all of the undetermined bits to 0, 1, or an intermediate value between 0 and 1. For example, the padding circuit 305 may set the most significant among the undetermined bits to 1 and set the remaining bits to 0. In a case in which the A/D conversion is not interrupted, the padding circuit 305 will directly output the supplied digital data bits. Instead of setting a fixed value to each undetermined bit, the padding circuit 305 may circulate the undetermined bits for each interruption of the A/D conversion. If all of the undetermined bits are to be 0 in a case in which the initial value of each bit of digital data is 0, the processing by the padding circuit 305 need not be performed. In such a case, the padding circuit 305 may be omitted.

[Normal Operation]

Figure 5:
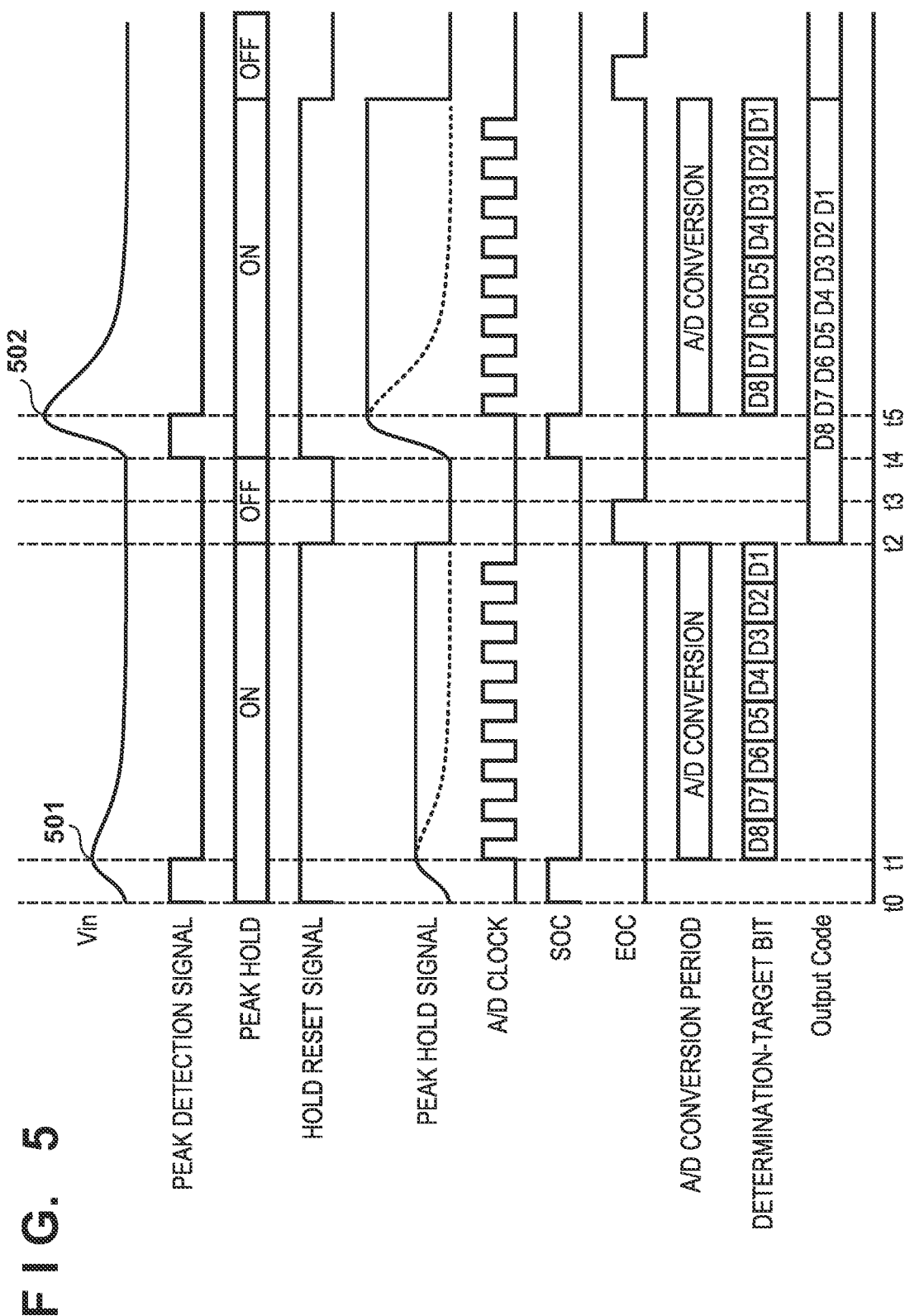
FIG. 5 is a timing chart for explaining an example of a normal operation according to the first embodiment.

An example of the operation of the signal processing circuit 123 will be described with reference to FIG. 5. FIG. 5 handles a case in which a pileup does not occur (that is, a case in which a time interval between two continuous peaks 501 and 502 is large and the generation of the peak 502 is detected after the end of the A/D conversion of the signal value of the peak 501). The operation of this case will be referred to as a normal operation. In the following description, assume that the resolution precision of the A/D conversion unit 202 is of 8 bits. In addition, in FIG. 5 and in the subsequent drawings, "Vin", "Peak Detection Signal", "Hold Reset Signal", "Peak Hold Signal", "SOC", and "EOC" indicate respective signal values. "Peak Hold" indicates whether the peak hold unit 302 is performing a peak hold operation. "ON" indicates that the peak hold operation is being performed, and "OFF" indicates that the peak hold operation is not being performed (that is, the peak hold unit is following the voltage signal Vin). "A/D Clock" indicates an operation clock signal of the A/D conversion unit 202. "A/D Conversion Period" indicates the period in which the A/D conversion unit 202 is executing the A/D conversion. "Determination-target Bit" indicates the bit to be determined by A/D conversion. Reference symbols D8 to D1 denote bits of digital data from the most significant bit MSB (Most Significant Bit) to the least significant bit LSB (Least Significant Bit). "Output Code" indicates the digital data to be output from the A/D conversion unit 202.

At time t0, assume that the voltage signal Vin has increased in accordance with the input of radiation photons. The peak detection circuit 126 detects, in accordance with this increase, that a peak will be generated and changes the peak detection signal and the hold reset signal to high. In response to the fact that the hold reset signal has changed to high, the peak hold unit 302 starts holding the voltage signal Vin. As shown in FIG. 5, while the hold reset signal is high, the value of the peak hold signal is set to the maximum value obtained up to the current point of time since time t0.

In response to the peak detection signal being changed to high, the control unit 201 changes the signal SOC to high. In response to the signal SOC being changed to high, the A/D conversion unit 202 prepares (initializes the A/D conversion unit 202) to start the A/D conversion.

At time t1, the peak detection unit 301 detects that the voltage signal Vin has reached the peak 501. In response to this, the peak detection signal is changed to low. In response to the peak detection signal being changed to low, the control unit 201 changes the signal SOC to low. In response to the signal SOC being changed to low, the A/D conversion unit 202 starts the A/D conversion of the peak hold signal. The value of the peak hold signal becomes the signal value of the peak 501 at the point of time t1.

During the A/D conversion, the SAR logic circuit 304 generates an A/D clock signal and supplies the generated A/D clock signal to the comparator 303. The SAR logic circuit 304 determines, in order from the most significant bit MSB (that is, the bit D8), the plurality of bits of digital data representing the signal value of the peak hold signal in synchronization with the A/D clock signal.

At time t2, the peak detection unit 301 detects that a predetermined time has elapsed from time t1 (that is, the voltage signal Vin has reached the peak 501), and changes the hold reset signal to low. This predetermined time is set in advance to be longer than the time required for the A/D conversion (that is, the time required to determine the bits D8 to D1) of the signal value of the peak 501. In response to the hold reset signal being changed to low, the peak hold signal ends the holding operation and starts to follow the voltage signal Vin.

In response to the hold reset signal being changed to low, the control unit 201 changes the signal EOC to high. In response to the signal EOC being changed to high, the A/D conversion unit 202 outputs the bits (that is, the bits D8 to D1) whose values have been determined as the digital data Output Code. The A/D conversion unit 202 may output the plurality of bits of the digital data Output Code in parallel.

At time t3, the control unit 201 changes the signal EOC to low upon detecting that a predetermined time has elapsed since time t2. At time t4, assume that the voltage signal Vin has started to increase in accordance with the input of the radiation photons. In response to this increase, the peak detection circuit 126 changes the peak detection signal and the hold reset signal to high. At time t5, the peak detection unit 301 detects that the voltage signal Vin has reached the peak 502. Subsequently, the signal value of the peak 502 undergoes A/D conversion in a manner similar to the A/D conversion of the signal value of the peak 501.

As described above, in a normal operation, the signal value of the peak 501 and the signal value of the peak 502 each undergo A/D conversion at an 8-bit precision.

[Pileup Operation]

Figure 6:
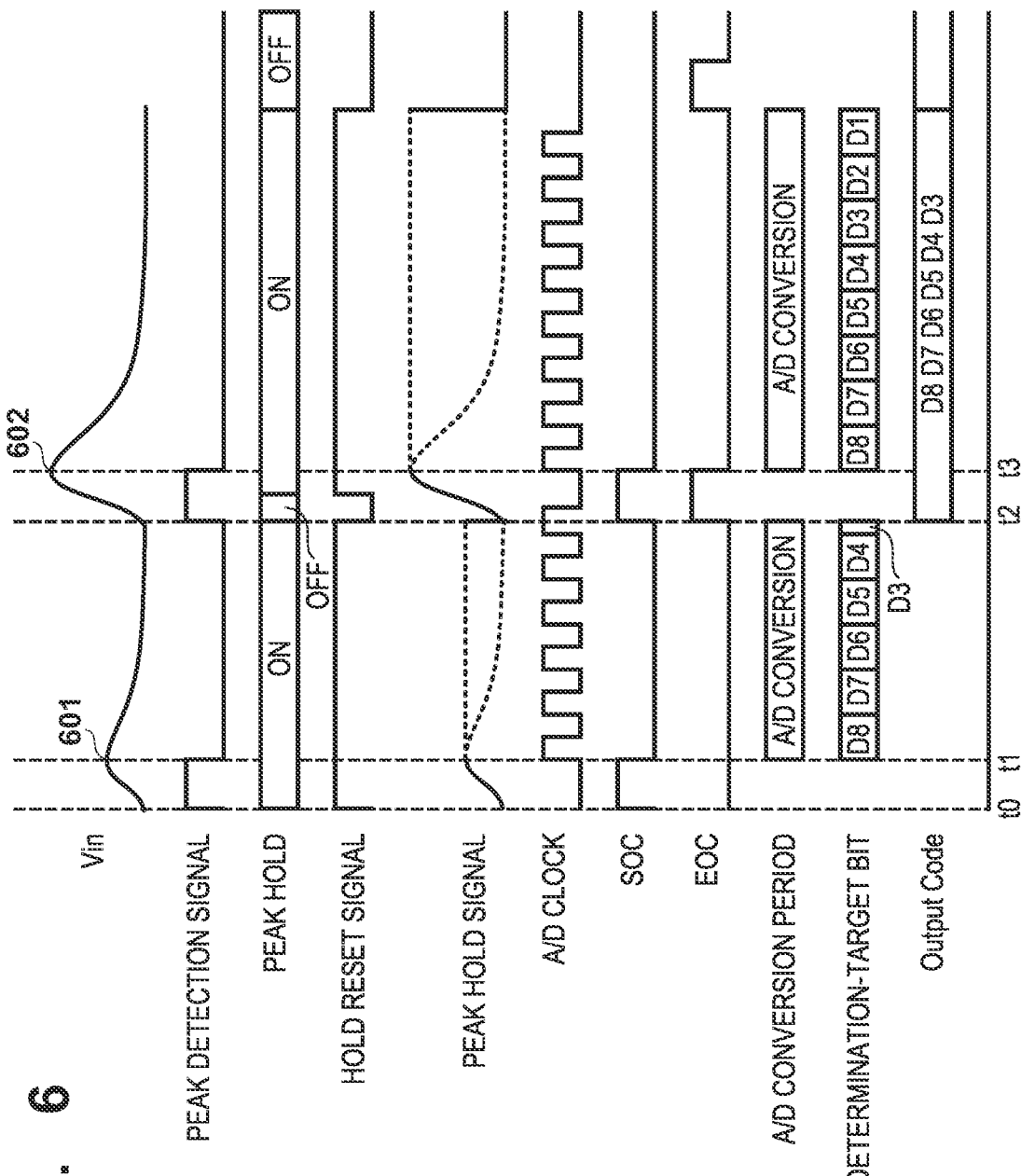
FIG. 6 is a timing chart for explaining an example of a pileup operation according to the first embodiment.

An example of the operation of the signal processing circuit 123 will be described with reference to FIG. 6. FIG. 6 shows a case in which a pileup occurs (that is, a case in which the time interval between two continuous peaks 601 and 602 is small, and the generation of the peak 602 is detected before the completion of the A/D conversion of the signal value of the peak 601). The operation performed in this case is referred to as a pileup operation.

The operation performed at time t0 and time t1 of FIG. 6 is similar to the operation performed at time t0 and time 1 of FIG. 5. In FIG. 6, the A/D conversion of the signal value of peak 601 is started at time t1.

At time t2, assume that the voltage signal Vin has started to increase in accordance with the input of the radiation photons during the A/D conversion of the signal value of the peak 601. In response to this increase, the peak detection circuit 126 changes the peak detection signal to high. In addition, the peak detection circuit 126 causes the hold reset signal to return to high after temporarily changing the hold reset signal to low. In response to the hold reset signal being temporarily changed to low, the peak hold unit 302 starts to newly hold the voltage signal Vin. As shown in FIG. 6, while the hold reset signal is high, the value of the peak hold signal is set to the maximum value obtained up to the current point of time since the hold reset signal has been changed to high.

In response to the peak detection signal being changed to high during the A/D conversion, the control unit 201 changes the signal SOC and the signal EOC to high. In response to the signal EOC being changed to high, the A/D conversion unit 202 interrupts the A/D conversion of the signal value of the peak 601 that is being currently executed, and supplies each bit whose value has been determined to the padding circuit 305. At the point of time t2, the A/D conversion of the signal value of the peak 601 has been completed for bits D8 to D3. Hence, the padding circuit 305 determines the values of the undetermined bits (the bits D2 and D1 in the above-described example) of the digital data of the peak 601 without basing them on the signal value (Vin) of the peak 601. The determination method of the undetermined bits is as described above. Subsequently, the padding circuit 305 outputs the bits D8 to D3 determined based on the signal value of the peak 602 and the complemented bits D2 and D1 as the digital data Output Code. In this manner, the peak 601 undergoes A/D conversion at a 6-bit precision.

In addition, in accordance with the signal SOC being changed to high, the A/D conversion unit 202 executes initialization for the A/D conversion of the signal value of the peak 602. In this manner, by executing the preparation for the A/D conversion at the point of time (t2) at which the voltage signal Vin is predicted to reach the peak 602, it will be possible to immediately start the A/D conversion of the signal value of the peak 602 after the voltage signal Vin has reached the peak 602.

At time t3, the control unit 201 changes the signal EOC to low upon detecting that a predetermined time has elapsed from time t2. In addition, at time t3, the peak detection unit 301 detects that the voltage signal Vin has reached the peak 602. Subsequently, the A/D conversion of the signal value of the peak 602 is started in a manner similar to the A/D conversion of the signal value of the peak 601. Although the voltage signal Vin reaches the peak 602 and the signal EOC is changed to low at the same time, they may occur at different times.

As described above, the signal value of the peak 601 whose A/D conversion was interrupted is converted into digital data at a 6-bit precision, and the signal value of the peak 602 whose A/D conversion was not interrupted is converted into digital data at an 8-bit precision. In this manner, according to this embodiment, even in a case in which a pileup occurs, both of the peaks 601 and 602 can be immediately counted by sacrificing the ADC resolution precision. Also, since only one signal value of a peak is held at one point of time, only the hold capacitor 407 need to be arranged as the capacitor for holding the signal value of a peak. In this manner, according to this embodiment, the counting performance can be improved by a simple arrangement (with low power consumption and small space).

Second Embodiment

[Outline of Operation]

In the first embodiment, A/D conversion was interrupted when the generation of the next peak was detected during the A/D conversion. However, if the A/D conversion operation is interrupted immediately after the start of the A/D conversion operation, the precision of the digital data to be output will decrease drastically. Hence, in the second embodiment, a control unit 201 determines whether to interrupt the A/D conversion based on the state of progress of the A/D conversion. Differences from the first embodiment will be mainly described below. Matters not mentioned in the second embodiment may be similar to those described in the above-described first embodiment.

Figure 7:
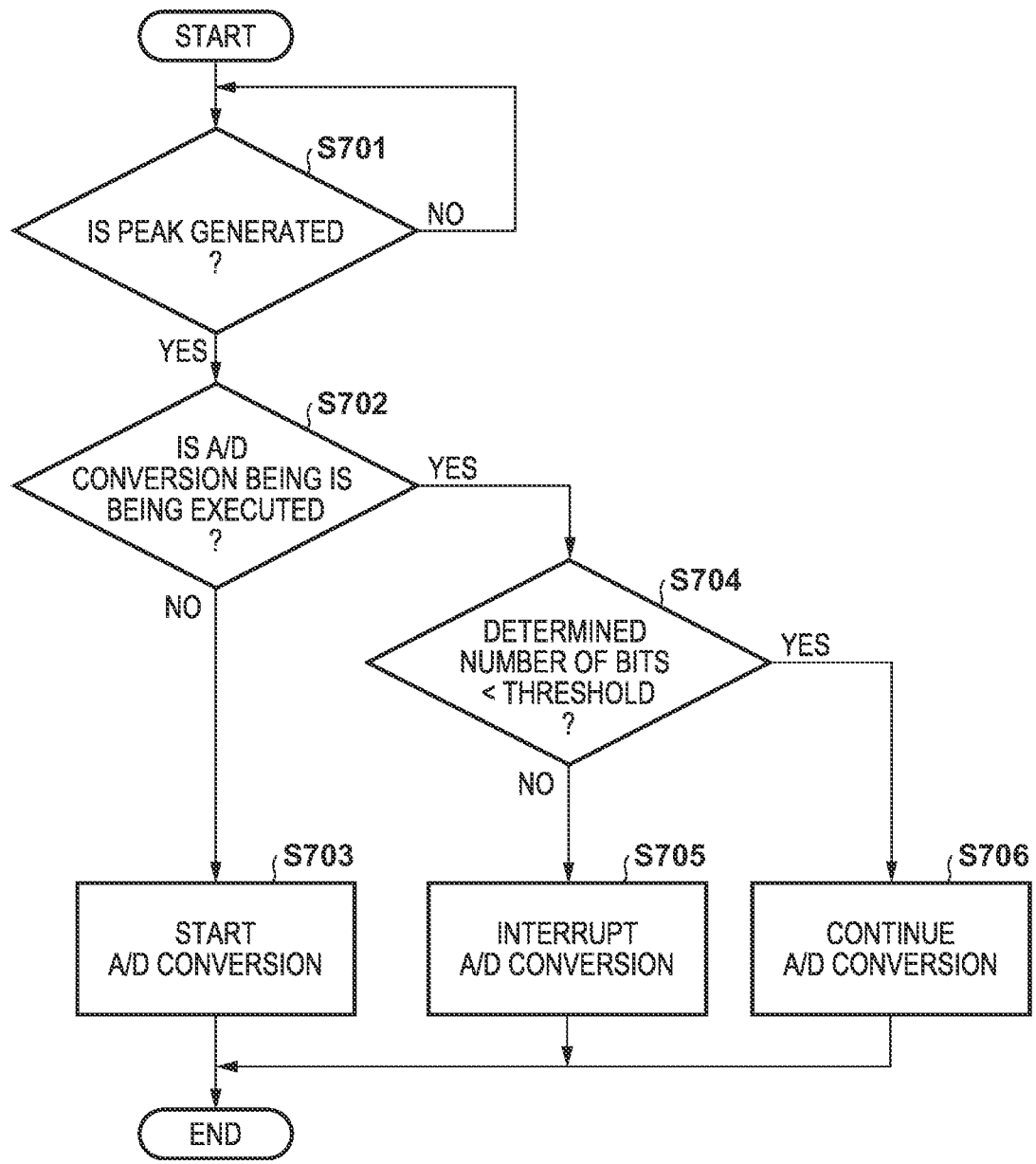
FIG. 7 is a flowchart for explaining an example of an operation according to the first embodiment.

The operation of the control unit 201 according to the second embodiment will be described with reference to FIG. 7. In step S701, the control unit 201 determines whether the generation of a peak has been detected. If the generation of a peak has been detected (YES in step S701), the control unit 201 advances the process to step S702. Otherwise (NO in step S701), the process of step S701 is repeated. As described above, the control unit 201 can detect the generation of a peak in response to a peak detection signal being changed to high.

In step S702, the control unit 201 determines whether A/D conversion is being executed. If A/D conversion is being executed (YES in step S702), the control unit 201 advances the process to step S704. Otherwise (NO in step S702), the process advances to step S703.

The A/D conversion of the preceding peak has already been completed if the process shifts to step S703. Hence, the control unit 201 will start the A/D conversion of the signal value of the newly reached peak.

In step S704, the control unit 201 determines whether the number of bits whose values have been determined is less than a threshold. If the number of bits whose values have been determined is less than the threshold (YES in step S704), the control unit 201 advances the process to step S706. Otherwise (the number of bits is equal to or more than the threshold) (NO in step S704), the process advances to step S705. The threshold to be used in step S704 is the smallest number of bits of precision permitted for the digital data which represents the signal value of this peak. This threshold is set in advance, and an A/D conversion circuit 127 can be used. The threshold may be a register signal which is set from a radiation imaging apparatus.

If the process shifts to step S705, a state in which digital data of minimum precision can be created will be set even though the A/D conversion of the preceding peak is being executed. Hence, the control unit 201 interrupts the A/D conversion in a manner similar to the pileup operation of the first embodiment.

If the process shifts to step S706, a state in which digital data of minimum precision cannot be created still will be set because the A/D conversion of the preceding peak is being executed. Hence, the control unit 201 continues the A/D conversion. In this case, the A/D conversion of the newly reached peak is not performed.

[Arrangement Example of A/D Conversion Circuit]

Figure 8:
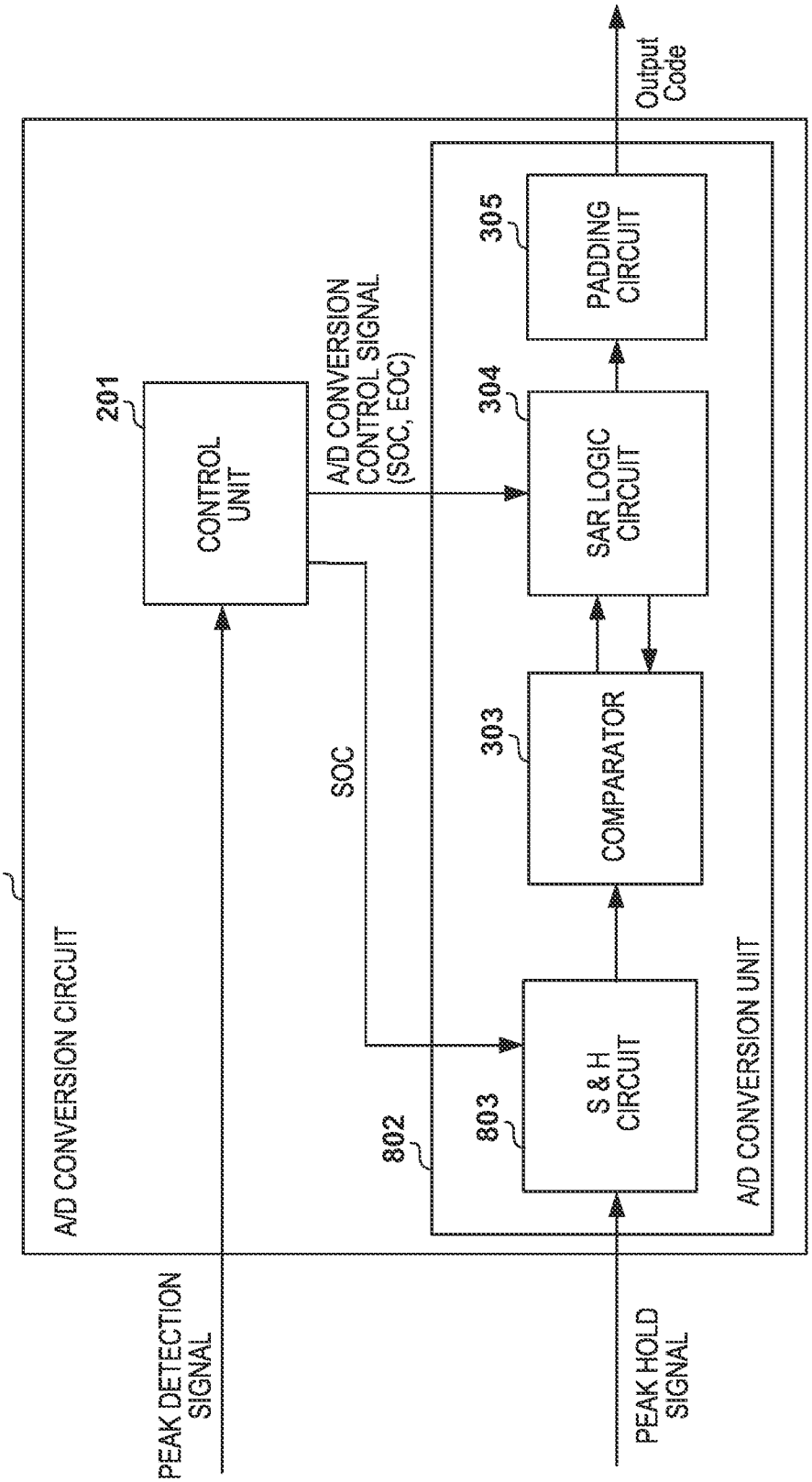
FIG. 8 is a block diagram for explaining an example of the arrangement of an A/D conversion circuit according to the second embodiment.

An example of the arrangement of an A/D conversion circuit 801 according to the second embodiment will be described with reference to FIG. 8. A radiation imaging apparatus according to the second embodiment differs from a radiation imaging apparatus 100 according to the first embodiment in that the A/D conversion circuit 801 is included instead of the A/D conversion circuit 127. Other points of the second embodiment may be similar to those of the first embodiment. The A/D conversion circuit 801 may also be used in the first embodiment.

The A/D conversion circuit 801 further includes a sample and hold circuit 803 (denoted as an S & H circuit in FIG. 8) in addition to the element of the A/D conversion circuit 127. A peak hold signal is supplied from a peak detection circuit 126 and a signal SOC is supplied from the control unit 201 to the sample and hold circuit 803. The sample and hold circuit 803 will sample the peak hold signal while the signal SOC is high, and hold the signal value at that point of time when the signal SOC changes to low. That is, the sample and hold circuit 803 functions as a holding unit.

[Normal Operation]

An example of the operation of a signal processing circuit 123 will be described with reference to FIG. 9. FIG. 7 shows a case in which the process of step S703 is executed. The operation of this case will be referred to as a normal operation. In the following description, assume that the resolution precision of an A/D conversion unit 202 is of 8 bits. In addition, in FIGS. 9 to 11, a "threshold signal" indicates a signal which is kept high for a length corresponding to the threshold of step S704. For example, assume that the threshold is 3 bits. In this case, after the start of the A/D conversion, the threshold signal will be kept high for the length (the length of three cycles of the A/D clock) required for the A/D conversion of 3 bits, and will be kept low in a period other than this. In the second embodiment, the hold reset signal has the same waveform as the peak detection signal. Hence, the hold reset signal will be omitted in FIGS. 9 to 11.

At time t0, assume that a voltage signal Vin has started to increase in accordance with the input of radiation photons. In response to this increase, the peak detection circuit 126 detects the generation of a peak, and changes the peak detection signal and the hold reset signal to high. In response to the hold reset signal being changed to high, a peak hold unit 302 starts holding the voltage signal Vin. As shown in FIG. 5, while the hold reset signal is high, the value of the peak hold signal is set to the maximum value obtained up to the current point of time since time t0.

In response to the peak detection signal being changed to high, the control unit 201 changes the signal SOC to high. In response to the signal SOC being changed high, the A/D conversion unit 202 prepares (initializes the A/D conversion unit 202) to start the A/D conversion.

At time t1, the peak detection unit 301 detects that the voltage signal Vin has reached a peak 501. In response to this, the peak detection signal and the peak hold signal are changed to low. In response to the hold reset signal being changed to low, the peak hold unit ends the holding operation and starts following the voltage signal Vin. Since the waveform of the peak hold signal will become similar to the waveform of the voltage signal Vin, a description will be omitted in FIGS. 9 to 11.

In response to the peak detection signal being changed to low, the control unit 201 changes the signal SOC to low. In response to the signal SOC being changed to low, the A/D conversion unit 202 holds the peak hold signal and starts the A/D conversion of the held signal value. In addition, the control unit 201 changes the threshold signal to high. At the point of time t1, the value of the peak hold signal is set as the signal value of a peak 901. The details of the A/D conversion are similar to those of the first embodiment.

The operations performed from time t2 to time t3 are similar to those of the first embodiment. At time t4, assume that the voltage signal Vin has started to increase in accordance with the input of radiation photons. In response to this increase, the peak detection circuit 126 changes the peak detection signal and the hold reset signal to high. In response to the peak detection signal being changed to high, the control unit 201 changes the signal SOC to high. In response to the signal SOC being changed to high, the A/D conversion unit 202 starts sampling the peak hold signal. At time t5, a peak detection unit 301 detects that the voltage signal Vin has reached a peak 902. Subsequently, the signal value of the peak 902 undergoes A/D conversion in a manner similar to the A/D conversion of the signal value of the peak 901.

As described above, in a normal operation, A/D conversion is performed on each of the signal value of the peak 901 and the signal value of the peak 902 at an 8-bit precision.

[Interruption Operation at Time of Pileup]

Figure 10:
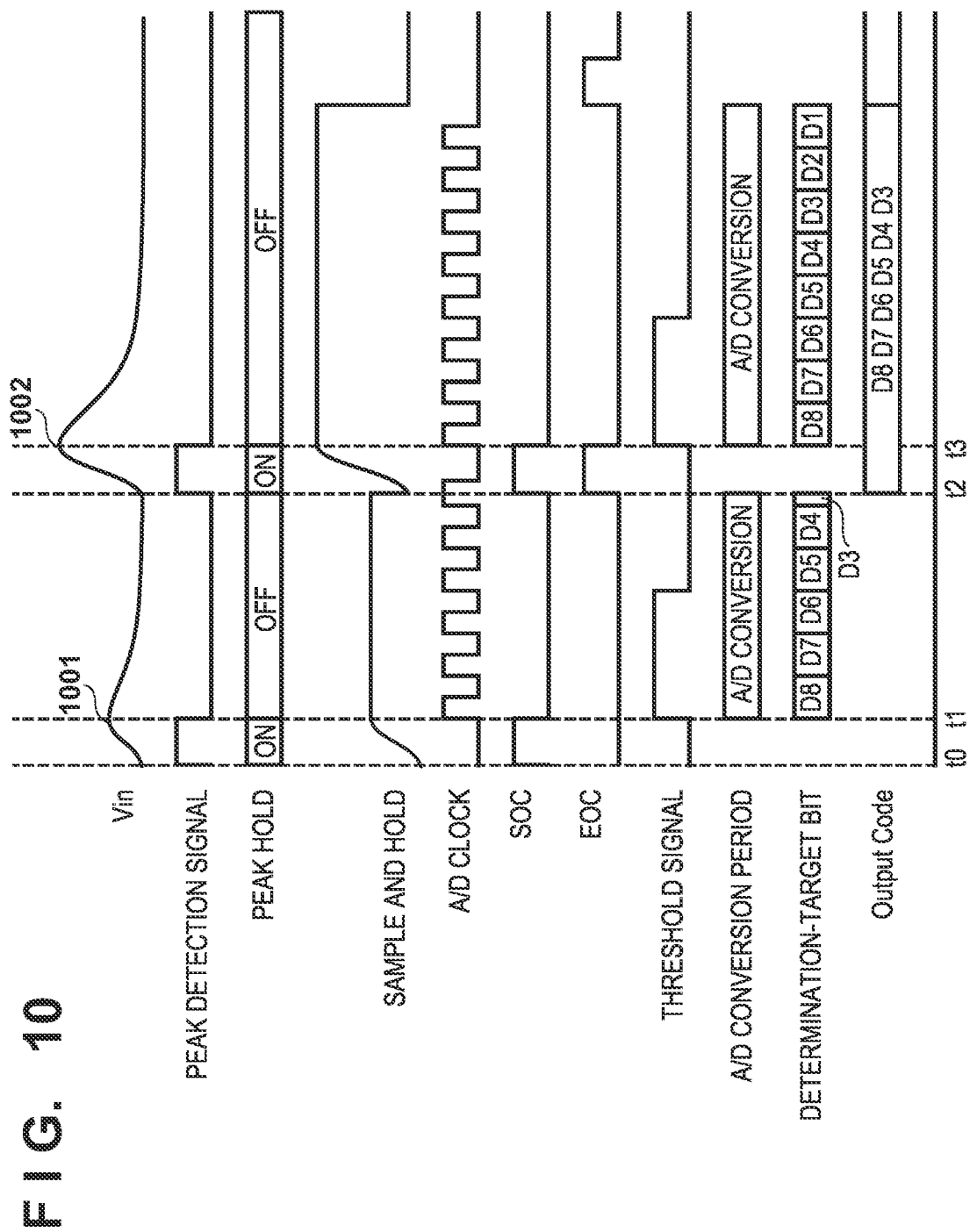
FIG. 10 is a timing chart for explaining an example of interruption operation according to the second embodiment.

An example of the operation of the signal processing circuit 123 will be described with reference to FIG. 10. FIG. 10 shows a case in which the process of step S705 of FIG. 7 is to be executed. The operation in this case will be referred to as an interruption operation at the time of a pileup.

Figure 9:
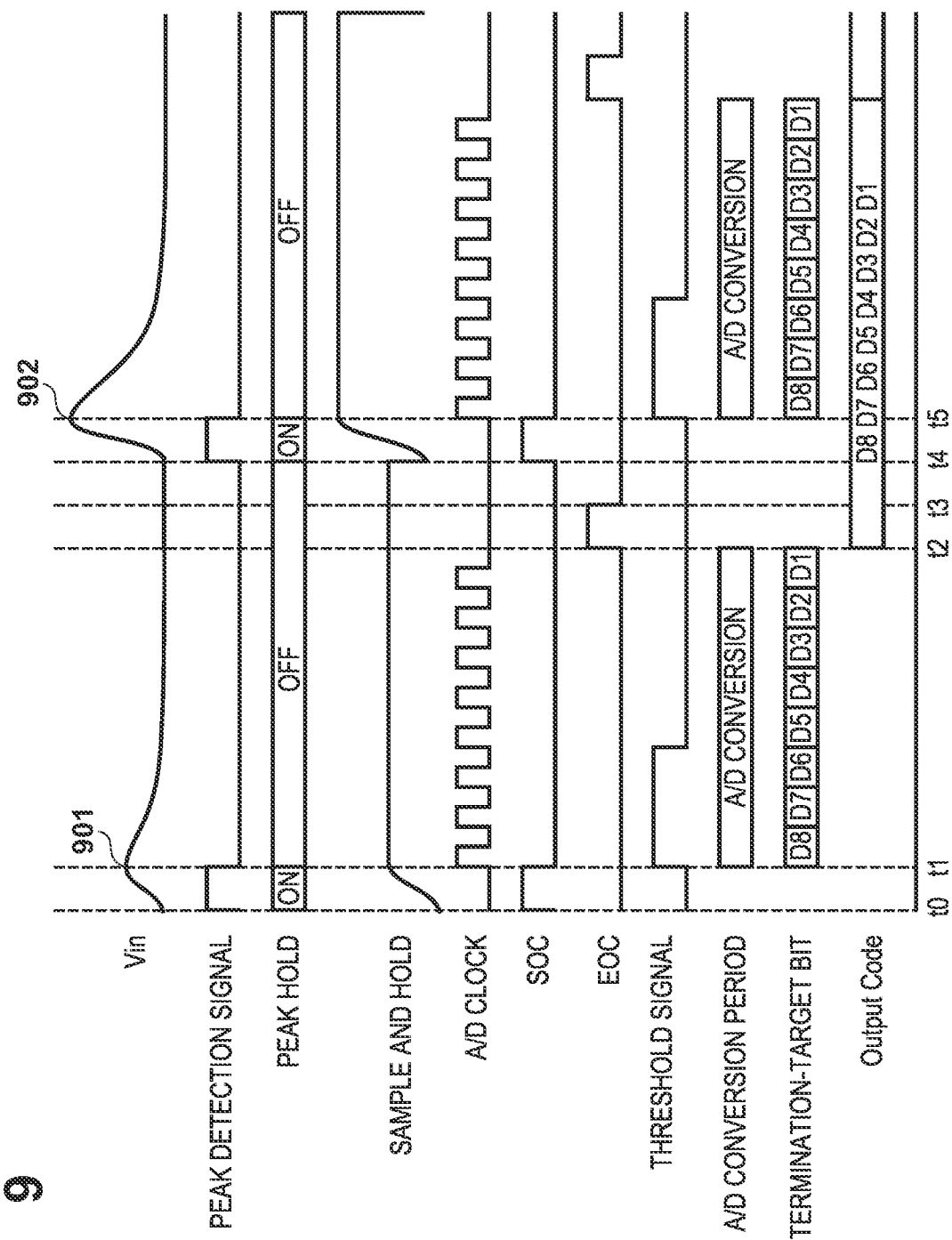
FIG. 9 is a timing chart for explaining an example of a normal operation according to the second embodiment.

The operations performed at time t0 and time t1 of FIG. 10 are similar to the operations performed at time t0 and time t1 of FIG. 9. In FIG. 10, the A/D conversion of the signal value of a peak 1001 is started at time t1.

At time t2, assume that the voltage signal Vin has started to increase in accordance with the input of the radiation photons during the A/D conversion of the signal value of the peak 1001. In response to this increase, the peak detection circuit 126 changes the peak detection signal to high.

In response to the peak detection signal being changed to high during the A/D conversion, the control unit 201 determines whether the threshold signal is high or low. A case in which the threshold signal is low represents that the process of step S704 in which whether the number of bits satisfies the threshold is determined has been completed. A case in which the threshold signal is high represents that the process of step S704 in which whether the number of bits satisfies the threshold is determined has not been completed. Since the threshold signal is low in the example of FIG. 10, the control unit 201 changes the signal SOC and a signal EOC to high to interrupt the A/D conversion of the signal value of the peak 1001. In response to the signal EOC being changed to high, the A/D conversion unit 202 interrupts the A/D conversion of the signal value of the peak 1001 which is being executed, and supplies the bits whose values have been determined to the padding circuit 305. The interruption operation is similar to that described in FIG. 6 of the first embodiment.

At time t3, the control unit 201 detects whether a predetermined time has elapsed from time t2 and changes the signal EOC to low. Also, at time t3, the peak detection unit 301 detects that the voltage signal Vin has reached a peak 1002. Subsequently, the A/D conversion of the signal value of the peak 1002 is started in a manner similar to the A/D conversion of the signal value of the peak 901. Although the voltage signal Vin reaches the peak 1002 at the same time as the time at which the signal EOC is changed to low, they may occur at different times.

[Continuation Operation at Time of Pileup]

Figure 11:
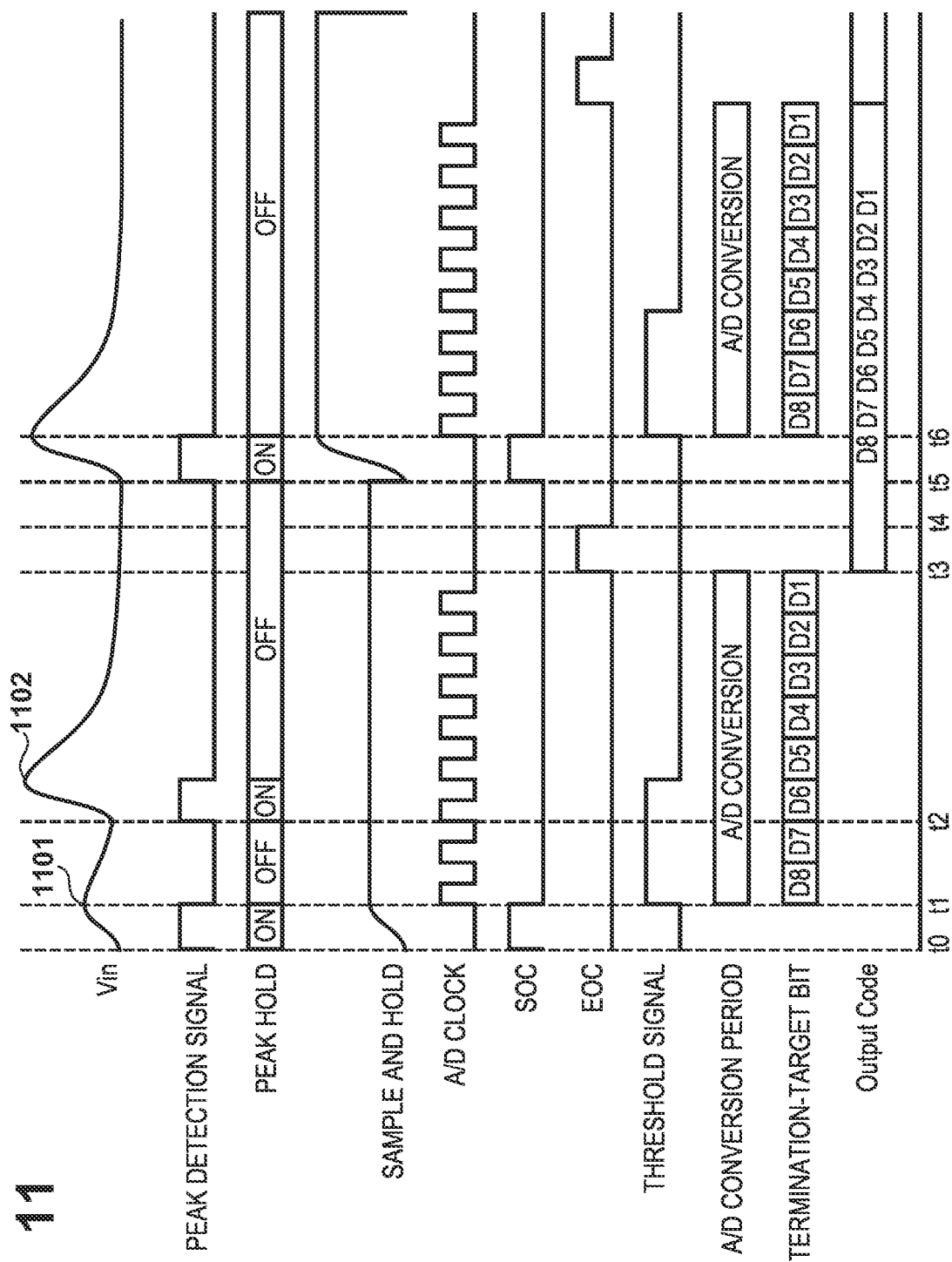
FIG. 11 is a timing chart for explaining an example of a continuation operation according to the second embodiment.

An example of the operation of the signal processing circuit 123 will be described with reference to FIG. 11. FIG. 11 shows a case in which the process of step S706 of FIG. 7 is executed. The operation in this case will be referred to as a continuation operation at the time of a pileup.

The operations performed at time t0 and time t1 of FIG. 11 are similar to the operations performed at time t0 and time t1 of FIG. 9. In FIG. 11, the A/D conversion of the signal value of a peak 1101 is started at time t1.

At time t2, assume that the voltage signal Vin has started to increase in accordance with the input of the radiation photons during the A/D conversion of the signal value of the peak 1101. In response to this increase, the peak detection circuit 126 changes the peak detection signal to high.

In response to the peak detection signal being changed to high during the A/D conversion, the control unit 201 determines whether the threshold signal is high or low. Since the threshold signal is high in the example of FIG. 11, the control unit 201 continues the A/D conversion of the signal value of the peak 1101 instead of interrupting the A/D conversion. As shown in FIG. 11, only two bits D8 and D7 have been determined at the point of time t2, and the number of bits is less than the threshold of 3 bits. Hence, the control unit 201 keeps the signal SOC and the signal EOC at low level. Subsequently, the A/D conversion of the peak 1101 is completed at time t3. The operations performed from time t3 to time t6 are similar to the operations performed from time t2 to time t5 of FIG. 9.

Since the A/D conversion of the signal value of the peak 1101 will be continued, the A/D conversion of a peak 1102 is skipped. The sample and hold circuit 803 can continue holding the signal value of the peak 1101 even after the value of the peak hold signal has changed after the detection of the generation of the peak 1102.

As described above, according to this embodiment, it is possible to improve the counting performance by a simple arrangement and to further ensure a minimum ADC resolution precision.

Third Embodiment

[Error Generated by Pileup]

A signal value error due to the generation of a pileup will be described with reference to FIG. 12. A graph 1201 shows the waveform of a voltage signal Vin of a case in which it is assumed that only the first input of photons has occurred. A graph 1202 shows the waveform of the voltage signal Vin of a case in which it is assumed that only the second input of photons has occurred. A graph 1203 shows the waveform of the voltage signal Vin of a case in which the first and second inputs of photons have actually occurred. The graph 1201 and the graph 1203 match at time t2 and in times preceding time t2. From time t2 to time t4, the value of the graph 1203 becomes the sum of the value of the graph 1201 and the value of the graph 1202. The graph 1202 and the graph 1203 match at time t4 and in subsequent times.

The first peak is reached at time t1 in the graph 1203, and the second peak is reached at time t3 in the graph 1203. The value of the graph 1203 at time t1 represents the signal value of the peak due to the first input of photons. However, the value of the graph 1203 at time t1 becomes greater than the signal value (the peak of the graph 1202) of the peak of the second input of photons. The signal value (the peak of the graph 1202) of the peak of the second input of photons is substantially equal to the value obtained by subtracting the value of the graph 1201 at time t3 from the second peak of the graph 1203. Hence, in the third embodiment, in the case of an occurrence of a pileup (more specifically, in the case of an interruption of the A/D conversion), the digital data representing the signal value of a subsequent peak will be corrected.

[Example of Arrangement of Signal Processing Circuit]

Figure 13:
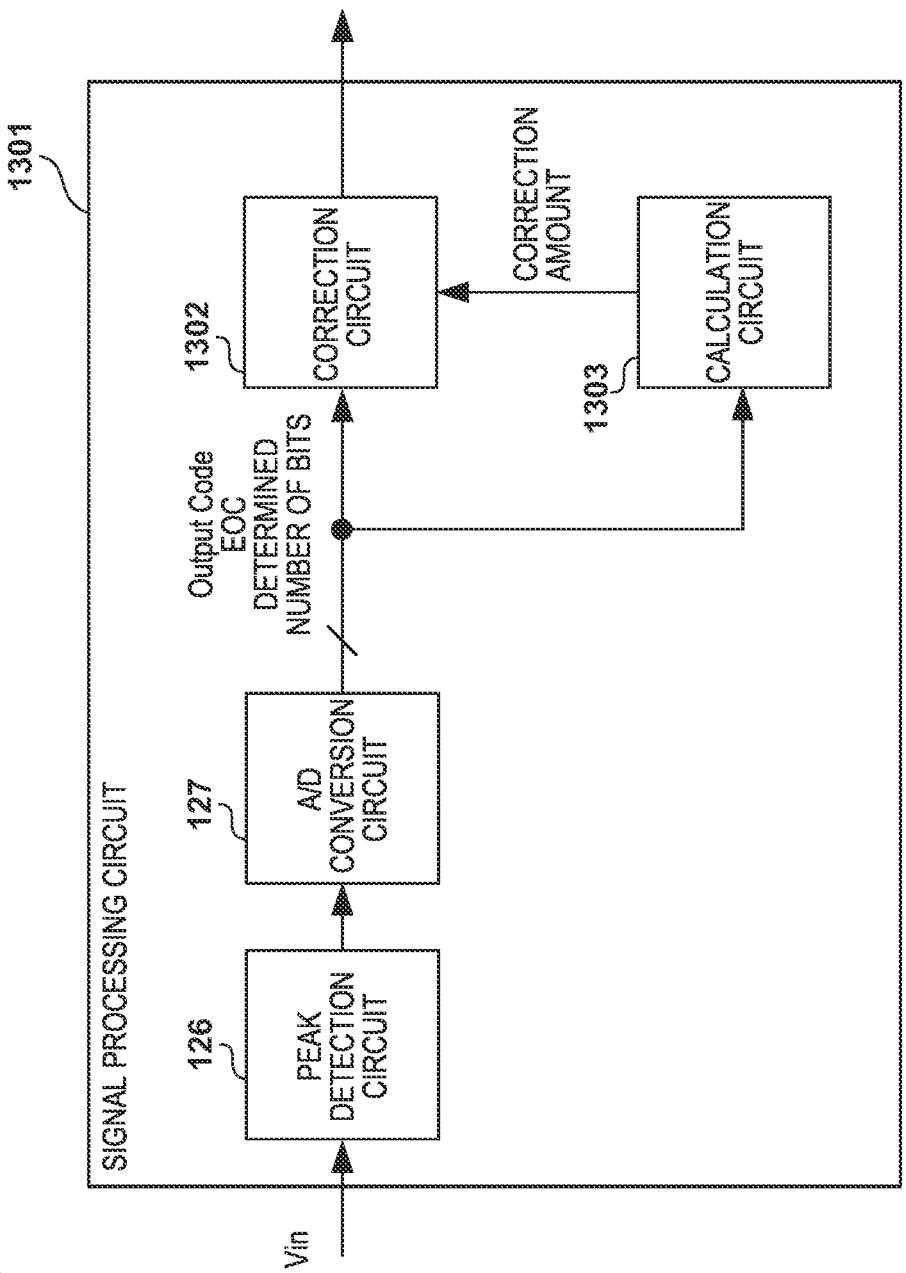
FIG. 13 is a block diagram for explaining an example of the arrangement of a signal processing circuit according to the third embodiment.

An example of the arrangement of a signal processing circuit 1301 according to the third embodiment will be described with reference to FIG. 13. A radiation imaging apparatus according to the third embodiment differs from a radiation imaging apparatus 100 according to the first embodiment in that the signal processing circuit 1301 is included instead of a signal processing circuit 123. Other points of the third embodiment may be similar to those of the first embodiment. The signal processing circuit 1301 may also be used in the second embodiment.

The signal processing circuit 1301 further includes a correction circuit 1302 and a calculation circuit 1303. The correction circuit 1302 and the calculation circuit 1303 function as a correction unit. The correction circuit 1302 corrects digital data Output Code. The calculation circuit calculates the correction amount to be used in the correction circuit 1302 and supplies the calculated correction amount to the correction circuit 1302. The digital data Output Code, a signal EOC, and the determined number of bits are supplied from an A/D conversion circuit 127 to each of the correction circuit 1302 and the calculation circuit 1303. The determined number of bits represents the number of bits whose values have been determined by the A/D conversion. For example, the determined number of bits in the A/D conversion of the signal value of a peak 501 of FIG. 5 is 8, and the determined number of bits in the A/D conversion of the signal value of a peak 601 of FIG. 6 is 6.

Based on the signal EOC, the correction circuit 1302 and the calculation circuit 1303 detect that the A/D conversion has been completed. In response to the completion of the A/D conversion, the calculation circuit 1303 calculates the correction amount for correcting the digital data Output Code. The correction circuit 1302 corrects the digital data Output Code by subtracting this correction amount from the digital data Output Code.

The calculation method of the correction amount by the calculation circuit 1303 will be described with reference to FIG. 14. The calculation circuit 1303 holds a table 1400. A column 1401 of the table 1400 represents the digital data that represents the signal value of the peak of the first half (the first peak) at the occurrence of a pileup. A column 1402 of the table 1400 represents the digital data representing the elapsed time since the peak of the first half (the first peak) has been reached at the occurrence of the pileup until the detection of the generation of the peak of the second half (the second peak). A column 1403 of the table 1400 represents the correction amount of the digital data representing the signal value of the peak of the second half (the second peak) at the occurrence of the pileup.

Figure 12:
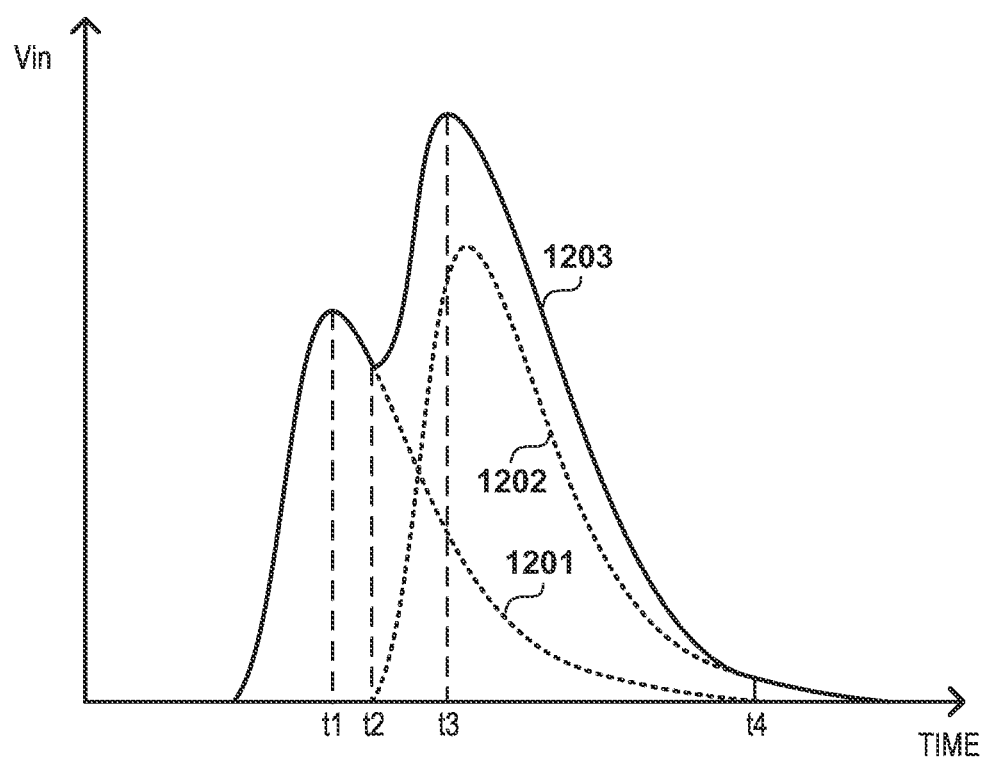
FIG. 12 is a graph for explaining error generation due to a pileup.

As shown in FIG. 12, the waveform of the voltage signal Vin of the case which assumes that only the first input of photons has occurred attenuates in accordance with a specific attenuation characteristic. Hence, the correction amount of the signal value of the peak generated by the second input of photons will change in accordance with the elapsed time since the voltage signal Vin has reached the peak (at time M. Since the A/D conversion of the signal value of the first peak is started at the point of time when the first peak has been reached, the above-described elapsed time corresponds to the execution time of the A/D conversion, that is, the number of bits determined in the A/D conversion. Hence, a correction amount will be determined in advance based on the digital data of the signal value of the peak of a preceding stage, the number of bits whose values have been determined in the A/D conversion of this signal value, and the attenuation characteristic of the voltage signal Vin, and the determined correction amount will be stored in the table 1400. The correction amount will be a positive value in a case in which the A/D conversion is interrupted (the value of the column 1402 is less than 8), and the correction amount will be 0 in a case in which the A/D conversion is completed (the value of the column 1402 is 8). The calculation circuit 1303 determines the correction amount by referring to the table 1400. Instead of referring to the table 1400, the calculation circuit 1303 may also calculate the correction amount by using a function that represents the attenuation characteristic.

As described above, according to this embodiment, the signal value of a peak can be calculated precisely even in a case in which a pileup has occurred.

Fourth Embodiment

[Example of Arrangement of Signal Processing Circuit]

Figure 15:
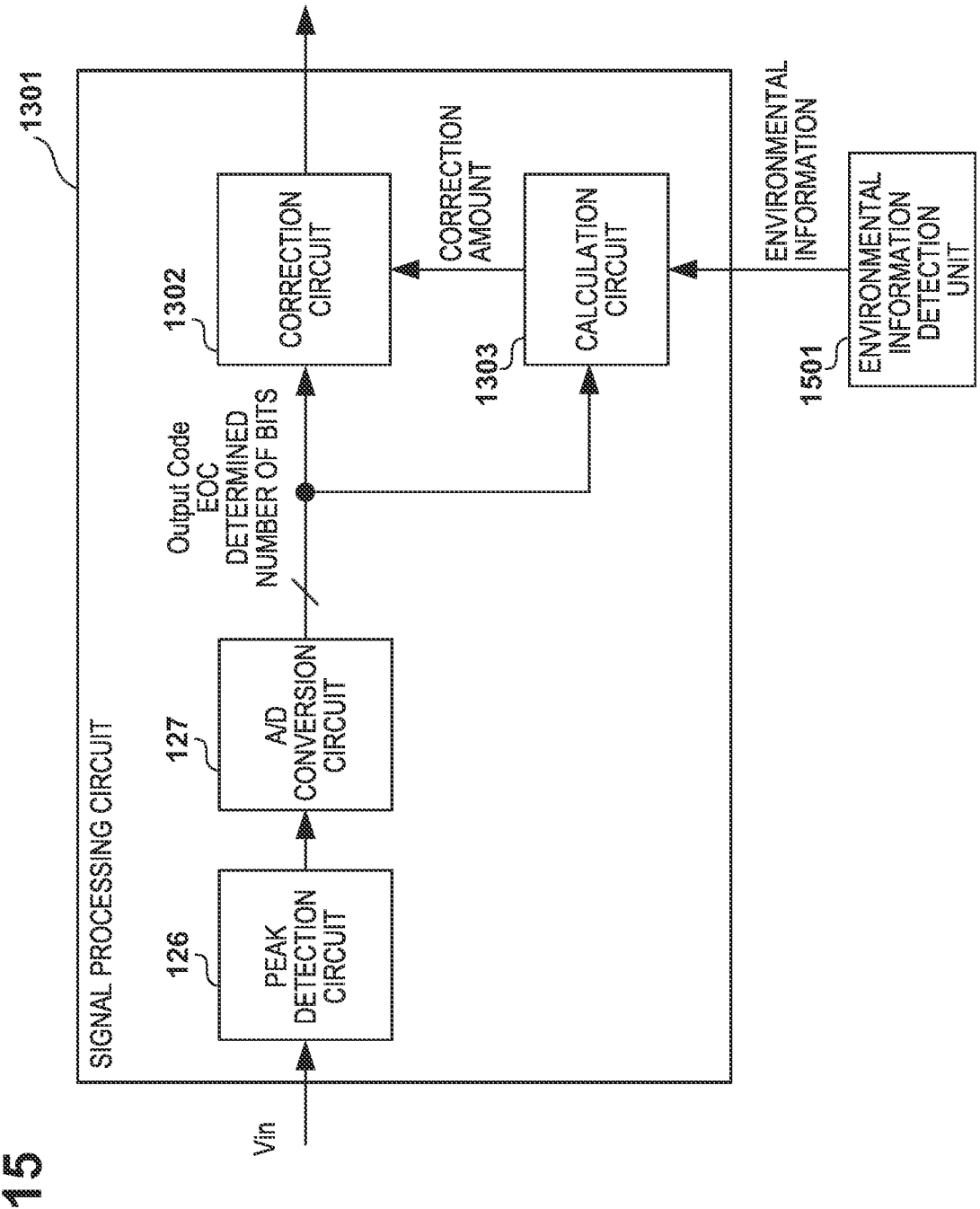
FIG. 15 is a block diagram for explaining an example of the arrangement of a signal processing circuit according to the fourth embodiment.

An example of the arrangement of a signal processing circuit 1301 according to the fourth embodiment will be described with reference to FIG. 15. The signal processing circuit 1301 according to this embodiment differs from the third embodiment in that a calculation circuit 1303 calculates a correction amount further based on the environmental information related to the signal processing circuit 1301. Other points may be similar to those of the third embodiment.

In the third embodiment, the correction amount was calculated based on an attenuation characteristic of a voltage signal Vin. This attenuation characteristic may change in accordance with the environmental information, for example, the individual differences of products, the peripheral temperature, and the like related to the signal processing circuit 1301. Hence, the calculation circuit 1303 obtains the environmental information from an environmental information detection unit 1501, and determines the correction amount further based on this environmental information. The calculation circuit 1303 may include a table 1400 shown in FIG. 14 or a conversion function for each attribute value (for example, the peripheral temperature) of environmental information, and use either the table or conversion function in accordance with each attribute value. The environmental information detection unit 1501 may be included in the radiation imaging apparatus 100. The environmental information detection unit 1501 may include a temperature sensor in a case in which the peripheral information is included in the environmental information. The environmental information detection unit 1501 may be included in the signal processing circuit 1301 or may be arranged outside of the signal processing circuit 1301.

As described above, according to this embodiment, the signal value of a peak can be determined further precisely even in a case in which a pileup has occurred.

Fifth Embodiment

Figure 16:
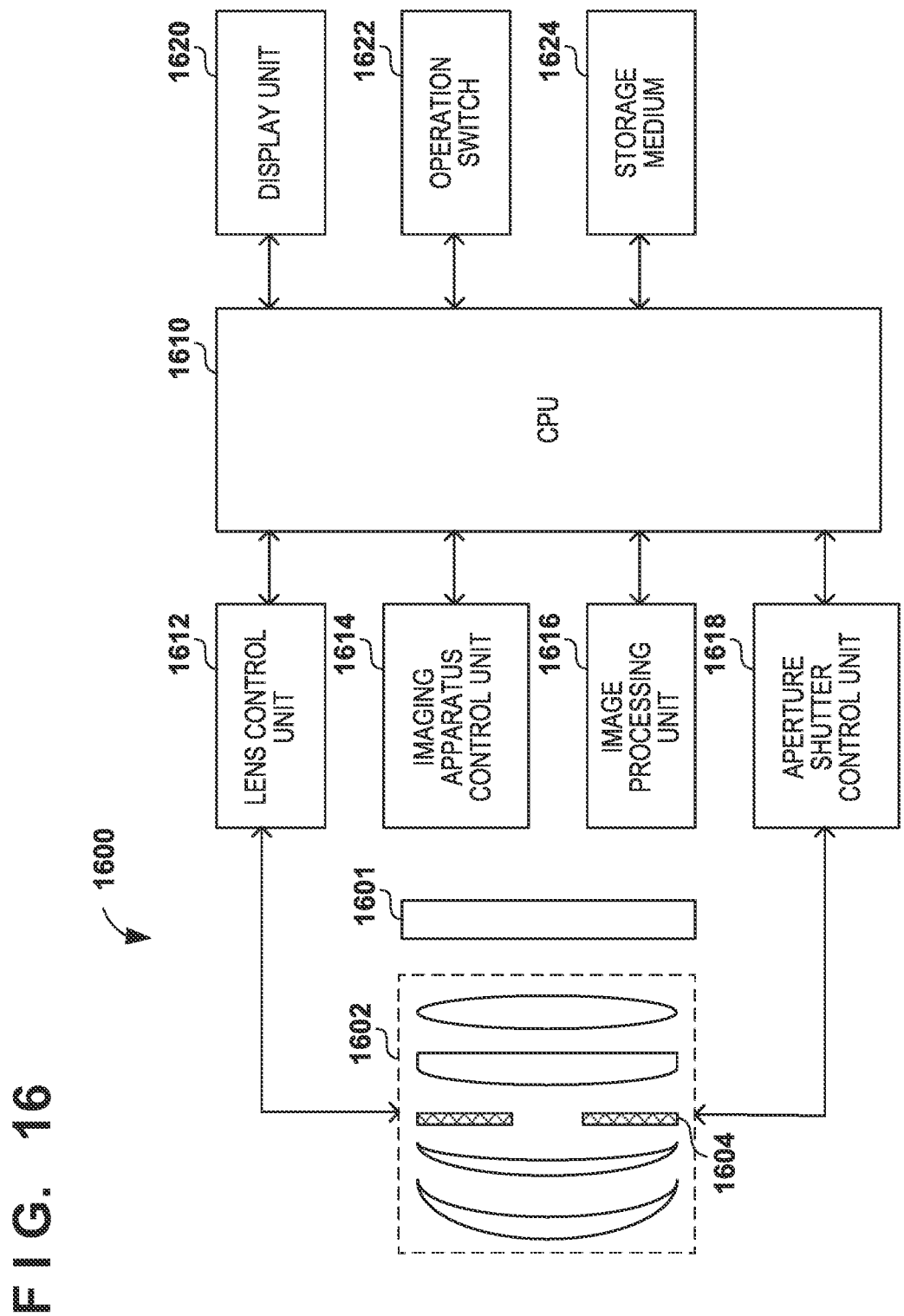
FIG. 16 is a block diagram for explaining an example of the arrangement of an imaging system according to the fifth embodiment.

An imaging system according to the fifth embodiment will be described with reference to FIG. 16. FIG. 16 is a block diagram showing a schematic arrangement of an imaging system according to this embodiment.

A photoelectric conversion device that includes a photon counting signal processing unit 120 according to each of the first embodiment to the fourth embodiment is provided. Such a photoelectric conversion device is applicable to various kinds of imaging systems. Applicable imaging systems include but are not limited to, for example, a digital still camera, a digital camcorder, a monitoring camera, a copy machine, a facsimile machine, a cell phone, an in-vehicle camera, an observation satellite, a medical camera, and the like. In addition, a camera module that includes an optical system such as a lens and a photoelectric conversion device can also be included as an imaging system. FIG. 16 shows a block diagram of a digital still camera as one example of these imaging systems.

An imaging system 1600 includes a photoelectric conversion device 1601, an imaging optical system 1602, a CPU 1610, a lens control unit 1612, an imaging apparatus control unit 1614, an image processing unit 1616, an aperture shutter control unit 1618, a display unit 1620, an operation switch 1622, and a storage medium 1624. The photoelectric conversion device 1601 includes the photon counting signal processing unit 120 according to each of the first embodiment to the fourth embodiment.

The imaging optical system 1602 is an optical system for forming an optical image of an object, and includes lenses, a stop 1604, and the like. The stop 1604 has, in addition to a function that adjusts the light amount at the time of imaging by adjusting its aperture size, a function as an exposure time adjustment shutter when a still image is to be captured. The lenses and the stop 1604 are held so as to be reciprocally movable along an optical axis direction, and a magnification function (zoom function) and a focus adjustment function are implemented by these cooperative movements. The imaging optical system 1602 may be integrated in the imaging system or may be an imaging lens which can be detached/attached from/to the imaging system.

The photoelectric conversion device 1601 is arranged in the image space of the imaging optical system 1602 so that the image plane will be positioned in the image space. The photoelectric conversion device 1601 includes a CMOS sensor (pixel unit) and a peripheral circuit (peripheral circuit region) thereof. The peripheral circuit includes the photon counting signal processing unit 120 according to each of the first embodiment to the fourth embodiment. The photoelectric conversion device 1601 forms a two-dimensional single-layer color sensor in which a plurality of pixels, which include photoelectric conversion units, are two-dimensionally arranged and a color filter is arranged with respect to these pixels. The photoelectric conversion device 1601 photoelectrically converts an object image formed by the imaging optical system 1602, and outputs the formed object image as an image signal and a focus detection signal.

The lens control unit 1612 is a unit for operating the magnification and adjusting the focus by controlling the reciprocal driving of the lenses of the imaging optical system 1602, and is formed by a circuit and a processing device which are formed to implement these functions. The aperture shutter control unit 1618 is a unit for adjusting the light amount for imaging by changing the aperture size of the stop 1604 (by changing the f-number), and is formed by a circuit and a processing device which are formed to implement this function.

The CPU 1610 is a control device that is arranged within the camera to govern various kind of control operations of the camera main body, and includes an operation unit, a ROM, a RAM, an A/D converter, a D/A converter, a communication interface circuit, and the like. The CPU 1610 controls the operation of each unit in the camera in accordance with a computer program stored in the ROM or the like, and executes a series of imaging operations such as autofocus control including detection (focus detection) of the focus state of the imaging optical system 1602, imaging, image processing, storing, and the like. The CPU 1610 is also a signal processing unit.

The imaging apparatus control unit 1614 is a unit for controlling the operation of the photoelectric conversion device 1601, and is formed by a circuit and a control device which are formed to implement this function. The image processing unit 1616 is a unit for generating an image signal by performing image processing such as color interpolation, γ conversion, and the like on an AD-converted signal, and is formed by a circuit and a control device which are formed to implement this function. The display unit 1620 is a display device such as a liquid crystal display device (LCD) or the like, and displays the information related to the imaging mode of the camera, a preview image before the imaging operation, an image used for confirmation after the imaging operation, the in-focus state at the time of focus detection, and the like. The operation switch 1622 is formed by a power supply switch, a release (imaging trigger) switch, a zoom operation switch, an imaging mode selection switch, and the like. The storage medium 1624 is a medium for storing a captured image and the like, and may be a medium incorporated in the imaging system or may be a detachable medium such as a memory card or the like.

In this manner, a high performance imaging system can be implemented by forming the imaging system 1600 in which the photon counting signal processing unit 120 according to each of the first embodiment to the fourth embodiment has been applied.

Sixth Embodiment

Figure 17A:
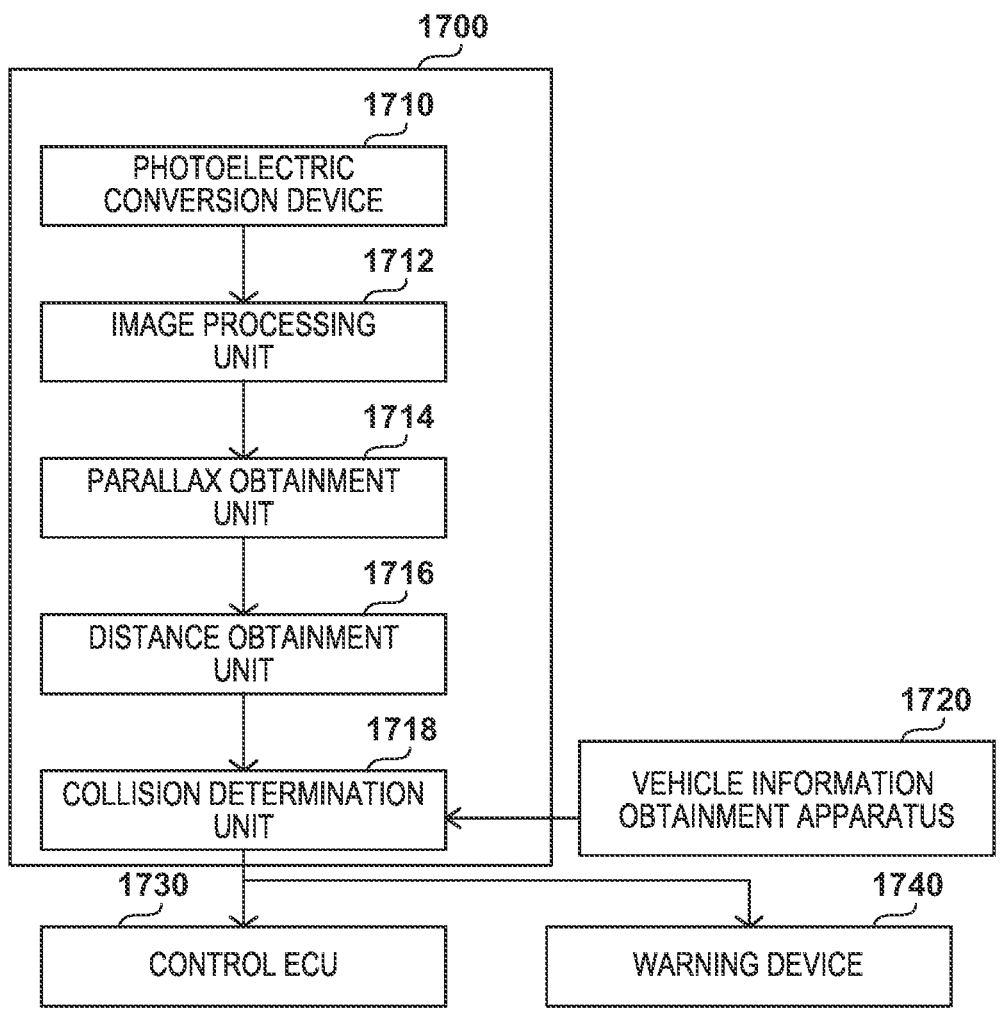
FIGS. 17A and 17B are block diagrams for explaining an example of the arrangement of a moving body according to the sixth embodiment.
Figure 17B:
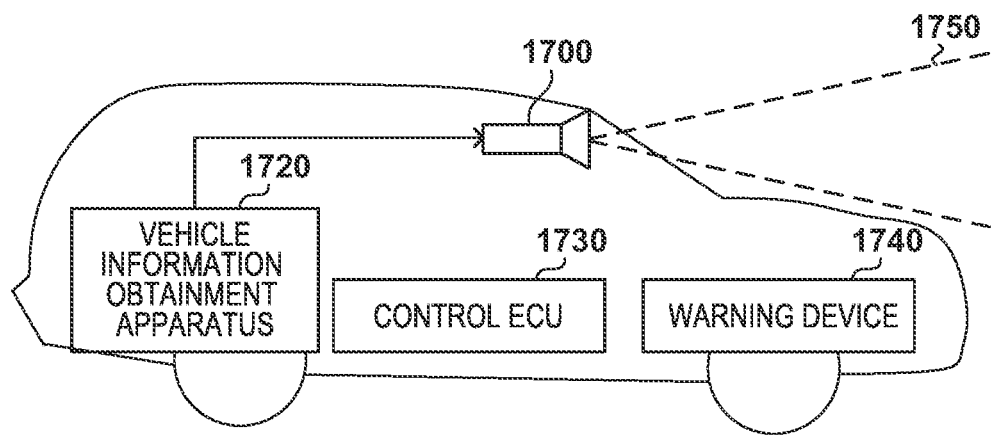

An imaging system and a moving body according to the sixth embodiment will be described with reference to FIGS. 17A and 17B. FIGS. 17A and 17B are views showing the arrangement of an imaging system and a moving body according to this embodiment.

FIG. 17A shows an example of an imaging system 1700 related to an in-vehicle camera. The imaging system 1700 includes a photoelectric conversion device 1710. The photoelectric conversion device 1710 includes a photon counting signal processing unit 120 according to each of the first embodiment to the fourth embodiment. The imaging system 1700 includes an image processing unit 1712 which is a processing device that performs image processing on a plurality of image data obtained by the photoelectric conversion device 1710. The imaging system 1700 also includes a parallax obtainment unit 1714 which is a processing device that calculates a parallax (the phase difference of parallax images) from the plurality of image data obtained by the photoelectric conversion device 1710. In addition, the imaging system 1700 includes a distance obtainment unit 1716 which is a processing device that calculates the distance to a target object based on the calculated parallax and a collision determination unit 1718 which is a processing device that determines the possibility of a collision based on the calculated distance. In this case, the parallax obtainment unit 1714 and the distance obtainment unit 1716 are examples of an information obtainment unit for obtaining information such as distance information to a target and the like. That is, the distance information is information about a parallax, a defocus amount, a distance to the target, and the like. The collision determination unit 1718 may determine the collision possibility using one of these pieces of distance information. Each of the various kinds of processing devices described above can be implemented by specially designed hardware or general-purpose hardware which performs arithmetic processing based on a software module. Alternatively, each processing device may be implemented by an FPGA (Field Programmable Gate Array) or an ASIC (Application Specific Integrated Circuit) or may be implemented by a combination thereof.

The imaging system 1700 is connected to a vehicle information obtainment apparatus 1720 and can obtain vehicle information such as a vehicle speed, a yaw rate, and a steering angle. The imaging system 1700 also connected to a control ECU 1730 that is a control device configured to output a control signal to generate a braking force to the vehicle based on the determination result of the collision determination unit 1718. That is, the control ECU 1730 is an example of a moving body control unit for controlling a moving body based on the distance information. In addition, the imaging system 1700 is also connected to a warning device 1740 that generates a warning to a driver based on the determination result of the collision determination unit 1718. For example, if the possibility of a collision is high as the determination result of the collision determination unit 1718, the control ECU 1730 performs vehicle control to avoid a collision or reduce damage by, for example, applying the brake, returning the accelerator, or suppressing the engine output. The warning device 1740 warns the user by, for example, generating a warning sound or the like, displaying warning information on the screen of a car navigation system or the like, or vibrating a seat belt or steering wheel.

In this embodiment, the imaging system 1700 captures the periphery, for example, the front or rear of the vehicle. FIG. 17B shows the imaging system 1700 in a case in which the front of the vehicle (imaging range 1750) is captured. The vehicle information obtainment apparatus 1720 sends an instruction to cause the imaging system 1700 to operate and perform imaging. By using the photoelectric conversion device 1710 which includes the photon counting signal processing unit 120 according to each of the first embodiment to the fourth embodiment, the imaging system 1700 according to this embodiment can improve the measurement accuracy.

An example in which control is performed to prevent a collision against another vehicle has been described above. However, the imaging system can also be applied to control in which automated driving is performed by following another vehicle or control in which automated driving is performed to prevent deviation from a lane. The imaging system can be applied not only to a vehicle such as a self-vehicle but also to, for example, a moving body (moving apparatus) such as a ship, an airplane, or an industrial robot. Moving devices of the moving body (moving apparatus) are various kinds of movement units such as an engine, a motor, wheels, a propeller, and the like. In addition, the imaging system can also be applied not only to a moving body but also to an equipment that widely uses object recognition, such as ITS (Intelligent Transport Systems) or the like.

The photoelectric conversion device may be a front-surface irradiation type photoelectric conversion device or a back-surface irradiation type photoelectric conversion device. The photoelectric conversion device can have a structure (stacked chip structure) formed by stacking a first semiconductor chip in which a plurality of photoelectric conversion elements are arranged and a second semiconductor chip in which peripheral circuits are arranged. Each peripheral circuit of the second semiconductor chip can be set as an array circuit corresponding to a pixel array of the first semiconductor chip. Also, each peripheral circuit of the second semiconductor chip can be set as a matrix circuit corresponding to a pixel or a pixel block of the first semiconductor chip. A through-silicon via (TSV), a wiring line arranged between the chips by directly bonding a conductor such as copper or the like, a connection by a micro-bump between chips, connection by wire bonding, or the like can be adopted as the connection between the first semiconductor chip and the second semiconductor chip. In a case in which a stacked chip structure is to be employed, the photon counting signal processing unit 120 can be arranged in the first semiconductor chip or the second semiconductor chip.

Seventh Embodiment

Figure 18:
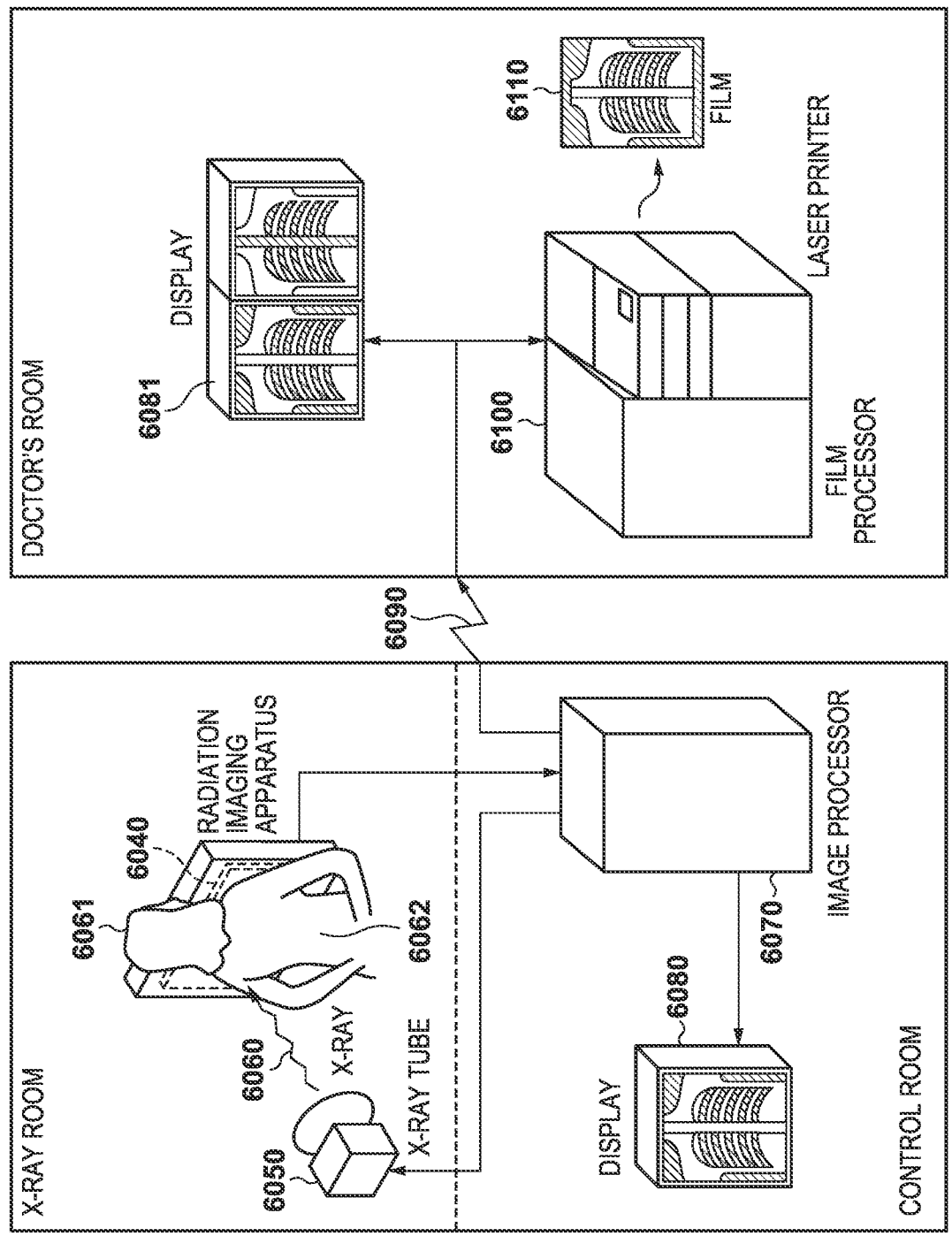
FIG. 18 is a block diagram for explaining an example of the arrangement of a radiation detection system according to the seventh embodiment.

FIG. 18 is a view showing an example in which a radiation detection apparatus according to this disclosure is applied to an X-ray diagnosis system (radiation detection system). X-rays 6060 generated by an X-ray tube 6050 (radiation source) pass through a chest 6062 of a patient or object 6061 and enter a detection apparatus 6040 that is formed by arranging a scintillator on the upper portion of the detection apparatus according to this disclosure. The detection conversion apparatus on which a scintillator is arranged on its upper portion forms a radiation detection apparatus in this case. The incident X-rays include the internal body information of the patient 6061. The scintillator emits light in correspondence the input of the X-rays, and the emitted light is photoelectrically converted to obtain electrical information. This electrical information is converted into a digital signal, undergoes image processing by an image processor 6070 serving as a signal processing unit, and can be observed on a display 6080 serving as a display unit in a control room. Note that the radiation detection system can include at least a detection apparatus and a signal processing unit for processing a signal from the detection apparatus.

Also, this information can be transferred to a remote place by a transmission processing unit such as a telephone line 6090 or the like. This allows the information to be displayed on a display 6081 serving as a display unit in a doctor's office in another place or to be stored in storage unit such as an optical disk or the like, and allows a doctor who is in a remote place to make a diagnosis. In addition, a film processor 6100 can also store the information on a film 6110 serving as a storage medium.

According to the above-described embodiments, the counting performance can be improved by a simple arrangement.

The present invention is not limited to the above embodiments and various changes and modifications can be made within the spirit and scope of the present invention. Therefore, to apprise the public of the scope of the present invention, the following claims are made.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2020-006220, filed Jan. 17, 2020, which is hereby incorporated by reference herein in its entirety.

What is claimed is:

1. A signal processing circuit comprising:
   a detection unit configured to detect generation of a peak in an analog signal whose signal value changes in accordance with an input of a photon;
   an A/D conversion unit configured to perform A/D conversion of a signal value of a peak of the analog signal into digital data of a plurality of bits by determining a value of each of the plurality of bits from an upper bit to a lower bit; and
   a control unit configured to control the A/D conversion unit so that, in a case in which the generation of a second peak of the analog signal is detected during a period between a timing of starting the A/D conversion of a signal value of a first peak of the analog signal and a timing of ending the A/D conversion of the signal value of the first peak of the analog signal, the A/D conversion of the signal value of the first peak will be interrupted and the A/D conversion of a signal value of the second peak will be started,
   wherein in a case in which the generation of the second peak of the analog signal is detected during the period between the timing of starting the A/D conversion of the signal value of the first peak of the analog signal and the timing of ending the A/D conversion of the signal value of the first peak of the analog signal, the A/D conversion of the signal value of the first peak is interrupted after a value of a first bit is determined in the A/D conversion of the signal value of the first peak and before a value of a second bit lower than the first bit is determined in the A/D conversion of the signal value of the first peak.

2. The circuit according to claim 1, wherein in a case in which the A/D conversion of the signal value of the first peak is interrupted, the A/D conversion unit determines digital data of the first peak based on one or more bits whose value has been determined.

3. The circuit according to claim 2, wherein the control unit determines, based on a progression state of the A/D conversion of the signal value of the first peak, whether to interrupt the A/D conversion of the signal value of the first peak in a case in which the generation of the second peak is detected.

4. The circuit according to claim 3, wherein in a case in which the number of bits whose values have been determined in the A/D conversion of the signal value of the first peak is less than a threshold, the control unit continues the A/D conversion of the signal value of the first peak, and
   in a case in which the number of bits whose values have been determined in the A/D conversion of the signal value of the first peak is not less than the threshold, the control unit interrupts the A/D conversion of the signal value of the first peak.

5. The circuit according to claim 2, wherein the control unit determines whether to interrupt the A/D conversion of the signal value of the first peak in a case in which the generation of the second peak is detected.

6. The circuit according to claim 1, wherein the control unit determines, based on a progression state of the A/D conversion of the signal value of the first peak, whether to interrupt the A/D conversion of the signal value of the first peak in a case in which the generation of the second peak is detected.

7. The circuit according to claim 6, wherein in a case in which a number of bits whose values have been determined in the A/D conversion of the signal value of the first peak is less than a threshold, the control unit continues the A/D conversion of the signal value of the first peak, and
   in a case in which the number of bits whose values have been determined in the A/D conversion of the signal value of the first peak is not less than the threshold, the control unit interrupts the A/D conversion of the signal value of the first peak.

8. The circuit according to claim 1, further comprising:
   a holding unit configured to hold the signal value of the first peak,
   wherein the holding unit can continue to hold the signal value of the first peak after the generation of the second peak has been detected.

9. The circuit according to claim 8, wherein the holding unit is a sample and hold circuit.

10. The circuit according to claim 1, further comprising:
   a correction unit configured to correct, in a case in which the A/D conversion of the signal value of the first peak is interrupted, second digital data representing the signal value of the second peak based on first digital data representing the signal value of the first peak and the number of bits whose values have been determined in the A/D conversion of the signal value of the first peak.

11. The circuit according to claim 10, wherein the correction unit determines a correction amount based on the first digital data, the number of bits determined in the A/D conversion of the signal value of the first peak, and an attenuation characteristic of the analog signal, and corrects the second digital data by subtracting the correction amount from the second digital data.

12. The circuit according to claim 10, wherein the correction unit corrects the second digital data further based on environmental information related to the signal processing circuit.

13. The circuit according to claim 1, wherein the A/D conversion unit is one of an SAR A/D conversion circuit, a cyclic A/D conversion circuit, and a pipeline A/D conversion circuit.

14. An imaging system comprising:
a signal processing circuit according to claim 1; and
a processing device configured to process a signal output from the signal processing circuit.

15. A moving body comprising:
a signal processing circuit according to claim 1;
a moving apparatus;
a processing apparatus configured to obtain information from a signal output from the signal processing circuit; and
a control apparatus configured to control the moving apparatus based on the information.

16. The circuit according to claim 1, wherein the control unit determines whether to interrupt the A/D conversion of the signal value of the first peak in a case in which the generation of the second peak is detected.

17. A signal processing method comprising:
detecting generation of a peak in an analog signal whose signal value changes in accordance with an input of a photon; and
performing A/D conversion of a signal value of a peak of the analog signal into digital data of a plurality of bits by determining a value of each of the plurality of bits from an upper bit to a lower bit,
wherein in the performing the A/D conversion, in a case in which the generation of a second peak of the analog signal is detected during a period between a timing of starting the A/D conversion of a signal value of a first peak of the analog signal and a timing of ending the A/D conversion of the signal value of the first peak of the analog signal, the A/D conversion of the signal value of the first peak will be interrupted and the A/D conversion of a signal value of the second peak will be started, and
wherein in a case in which the generation of the second peak of the analog signal is detected during the period between the timing of starting the A/D conversion of the signal value of the first peak of the analog signal and the timing of ending the A/D conversion of the signal value of the first peak of the analog signal, the A/D conversion of the signal value of the first peak is interrupted after a value of a first bit is determined in the A/D conversion of the signal value of the first peak and before a value of a second bit lower than the first bit is determined in the A/D conversion of the signal value of the first peak.

\* \* \* \* \*